Figure 1:
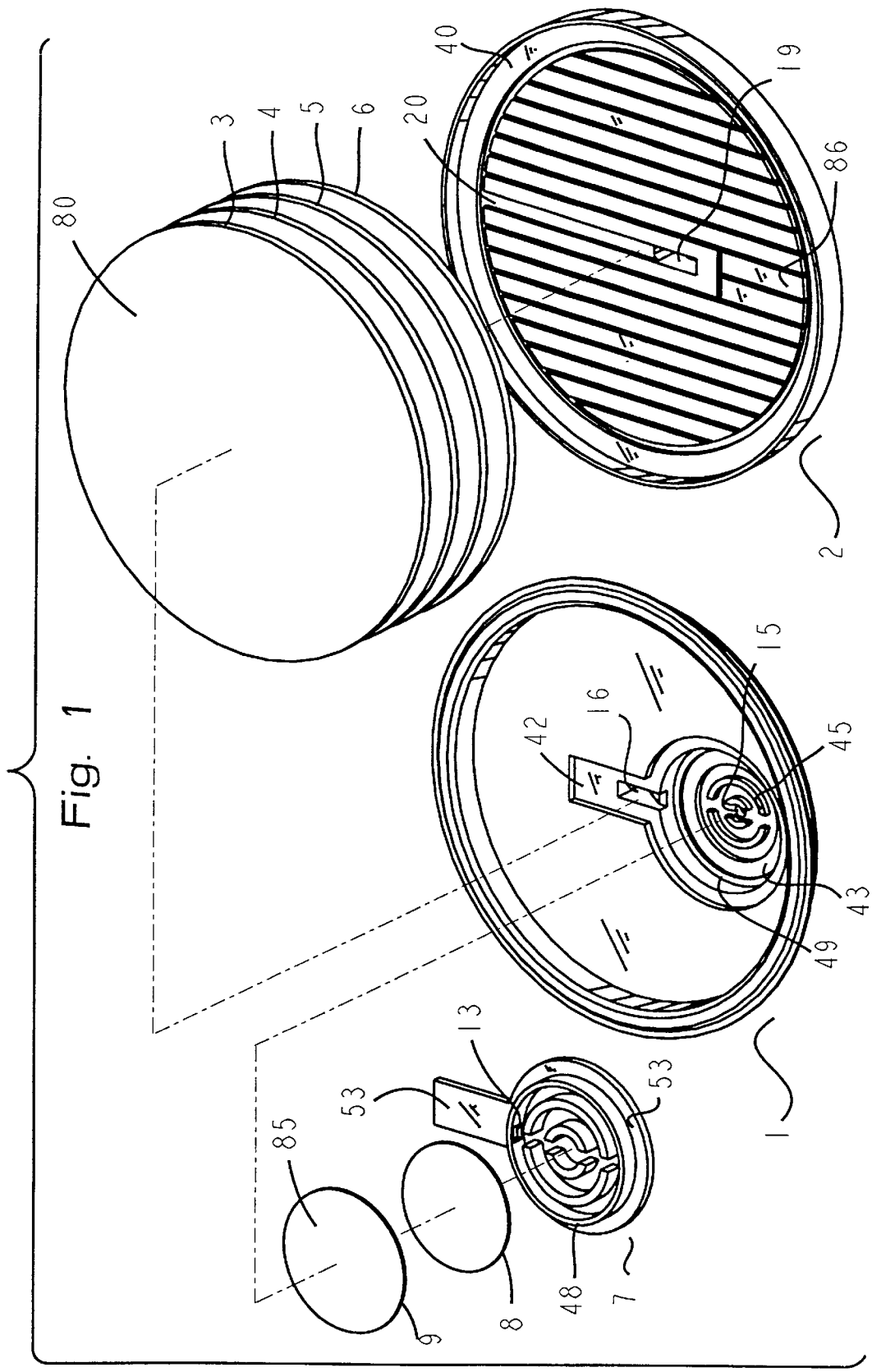

United States Patent [19]
Zuk, Jr. et al.

[11] Patent Number: 6,010,633
[45] Date of Patent: *Jan. 4, 2000

[54] METHOD OF PREVENTING AIR FROM BECOMING ENTRAPPED WITHIN A FILTRATION DEVICE

[75] Inventors: Peter Zuk, Jr., Harvard, Mass.; Jonathan C. Alt, Woodbury, Conn.

[73] Assignee: Hemasure Inc., Marlborough, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/812,717

[22] Filed: Mar. 6, 1997

[51] Int. Cl.⁷ .............................. B01D 37/00; B01D 24/24
[52] U.S. Cl. ...................... 210/767; 210/416.1; 210/436; 210/472
[58] Field of Search ..................................... 210/650, 767, 210/435, 436, 456, 472, 498, 416.1

[56] References Cited

U.S. PATENT DOCUMENTS

| | | | |
|---|---|---|---|
| 1,844,342 | 2/1932 | Berman . | |
| 2,073,991 | 3/1937 | Koser . | |
| 2,665,009 | 1/1954 | Harstick | 210/158 |
| 2,668,533 | 2/1954 | Evans | 128/214 |
| 2,784,843 | 3/1957 | Braunlich | 210/164 |
| 3,523,408 | 8/1970 | Rosenberg | 55/159 |
| 3,556,302 | 1/1971 | Agranat | 210/321 |
| 3,560,377 | 2/1971 | Loeffler | 210/456 |
| 3,593,854 | 7/1971 | Swank | 210/436 |
| 3,631,654 | 1/1972 | Riely et al. | 210/500 |
| 3,803,810 | 4/1974 | Rosenberg | 55/159 |
| 3,881,640 | 5/1975 | Noble | 222/158 |
| 3,892,236 | 7/1975 | Djerassi | 128/214 R |
| 3,935,110 | 1/1976 | Schmid et al. | 210/445 |
| 3,967,620 | 7/1976 | Noiles | 128/214 C |
| 4,009,715 | 3/1977 | Forberg et al. | 128/214 R |
| 4,038,191 | 7/1977 | Davis et al. | 210/321 B |
| 4,113,627 | 9/1978 | Leason | 210/446 |
| 4,126,558 | 11/1978 | Luceyk | 210/429 |
| 4,159,954 | 7/1979 | Gangemi | 210/446 |
| 4,170,056 | 10/1979 | Meyst et al. | 29/163.5 F |
| 4,229,306 | 10/1980 | Hein et al. | 210/446 |
| 4,276,170 | 6/1981 | Vaillancourt | 210/436 |
| 4,294,594 | 10/1981 | Sloane, Jr. et al. | 210/436 |
| 4,298,358 | 11/1981 | Ruschke | 210/436 |
| 4,320,001 | 3/1982 | Le Boeuf | 210/120 |
| 4,341,538 | 7/1982 | Vadnay et al. | 55/159 |
| 4,416,050 | 11/1983 | Sarace | 29/571 |
| 4,416,777 | 11/1983 | Kuroda et al. | 210/446 |
| 4,515,606 | 5/1985 | de Winter | 55/159 |
| 4,525,182 | 6/1985 | Rising et al. | 210/436 |
| 4,568,366 | 2/1986 | Frederick et al. | 210/436 |
| 4,631,050 | 12/1986 | Reed et al. | 604/4 |
| 4,675,383 | 6/1987 | Bohlen et al. | 530/351 |
| 4,828,587 | 5/1989 | Baurmeister et al. | 210/436 |
| 4,880,548 | 11/1989 | Pall et al. | 210/767 |
| 4,894,152 | 1/1990 | Colvin, Jr. et al. | 210/198.2 |
| 4,895,806 | 1/1990 | Le et al. | 435/288 |
| 4,906,260 | 3/1990 | Emheiser et al. | 55/159 |
| 4,925,572 | 5/1990 | Pall | 210/767 |

(List continued on next page.)

FOREIGN PATENT DOCUMENTS

| | | |
|---|---|---|
| 0 406 485 A1 | 1/1991 | European Pat. Off. . |
| 0 500 472 A2 | 8/1992 | European Pat. Off. . |
| 62-243561 | 10/1987 | Japan . |

*Primary Examiner*—John Kim
*Attorney, Agent, or Firm*—Heslin & Rothenberg, P.C.

[57] ABSTRACT

An in-line gravity filtration device for biological fluids such as blood or blood products is disclosed. The device includes a series of channels formed downstream of filtration elements. The channels are defined in cross sectional area by the distance between the filtration elements and their bottoms. The channels are configured to form flow paths to an outlet port so that air within the channels is forced downstream through the outlet port thereby minimizing air being trapped on the downstream side of the device. For optimum performance, the cross section area of a single continuous channel, or the sum of the cross sectional area of parallel channels, leading to a single outlet port, should not exceed the cross sectional area of the outlet port.

26 Claims, 18 Drawing Sheets

U.S. PATENT DOCUMENTS

| | | | |
|---|---|---|---|
| 4,936,998 | 6/1990 | Nishimura et al. | 210/638 |
| 4,943,287 | 7/1990 | Carmen | 604/408 |
| 4,944,876 | 7/1990 | Miller | 210/321.75 |
| 4,997,577 | 3/1991 | Stewart | 210/767 |
| 5,002,054 | 3/1991 | Ash et al. | 128/635 |
| 5,045,096 | 9/1991 | Quang et al. | 210/436 |
| 5,092,996 | 3/1992 | Spielberg | 210/232 |
| 5,126,045 | 6/1992 | Kohlheb et al. | 210/321.85 |
| 5,126,054 | 6/1992 | Matkovich | 210/641 |
| 5,143,630 | 9/1992 | Rolchigo | 210/780 |
| 5,156,602 | 10/1992 | Steffler | 604/319 |
| 5,171,439 | 12/1992 | Vakharia | 210/172 |
| 5,234,585 | 8/1993 | Zuk, Jr. | 210/188 |
| 5,252,222 | 10/1993 | Matkovich et al. | 210/650 |
| 5,258,127 | 11/1993 | Gsell et al. | 210/767 |
| 5,316,678 | 5/1994 | Heaslip | 210/486 |
| 5,360,545 | 11/1994 | Pall et al. | 210/505 |
| 5,380,437 | 1/1995 | Bertoncini | 210/416.1 |
| 5,429,742 | 7/1995 | Gutman et al. | 210/321.75 |
| 5,437,655 | 8/1995 | Bartholomew | 604/406 |
| 5,439,587 | 8/1995 | Stankowski et al. | 210/321.64 |
| 5,451,321 | 9/1995 | Matkovich | 210/641 |
| 5,454,951 | 10/1995 | Hoopman | 210/650 |
| 5,468,388 | 11/1995 | Goddard et al. | 210/321.75 |
| 5,470,488 | 11/1995 | Matkovich et al | 210/767 |
| 5,472,605 | 12/1995 | Zuk, Jr. | 210/436 |
| 5,472,621 | 12/1995 | Matkovich et al. | 210/767 |
| 5,536,405 | 7/1996 | Myrna et al. | 210/321.75 |
| 5,536,413 | 7/1996 | Bormann et al. | 210/650 |
| 5,545,339 | 8/1996 | Bormann et al. | 210/806 |
| 5,630,939 | 5/1997 | Bulard et al. | 210/416.1 |
| 5,639,376 | 6/1997 | Lee et al. | 210/645 |
| 5,827,429 | 10/1998 | Ruschke et al. | 210/435- |

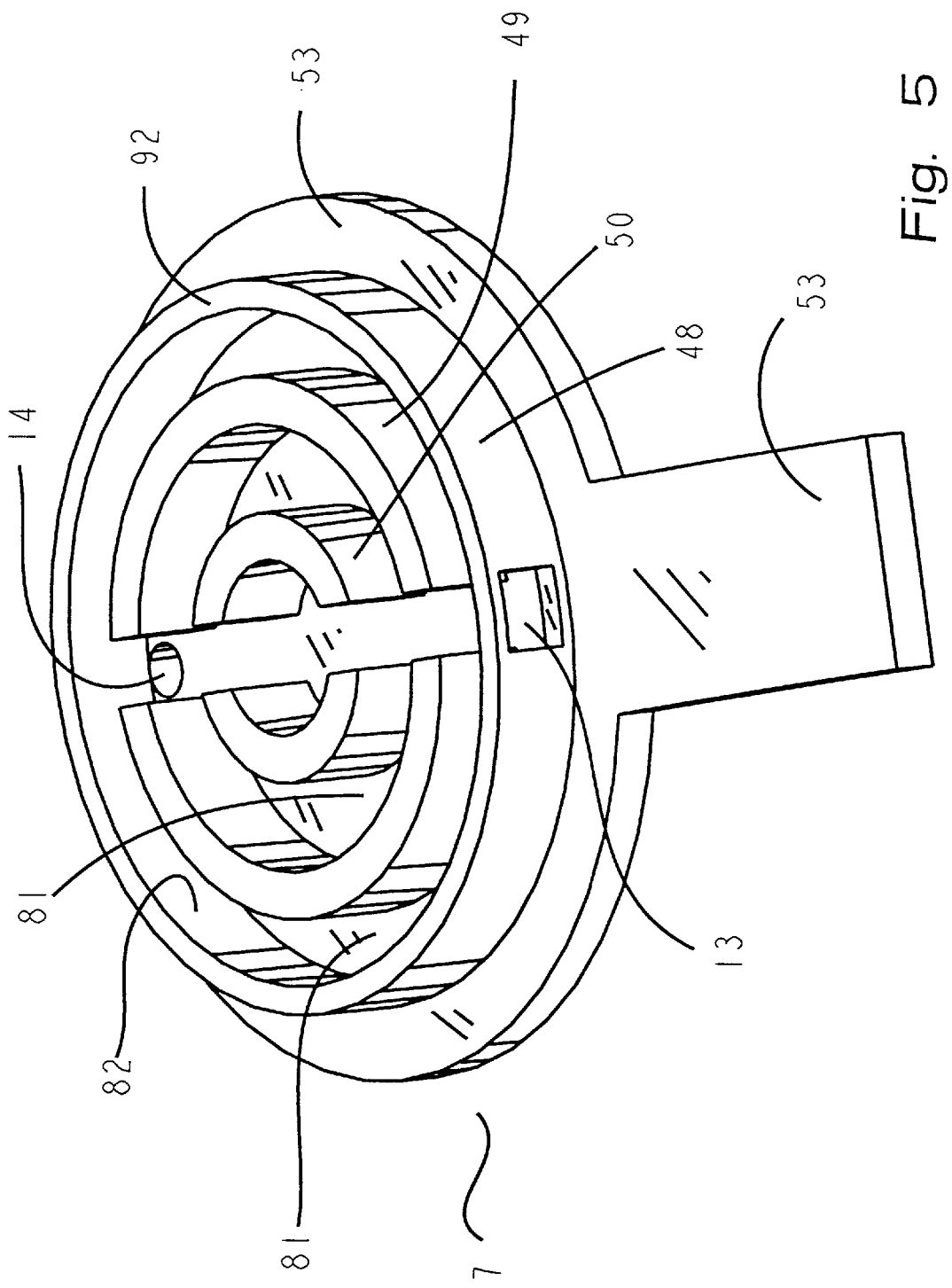

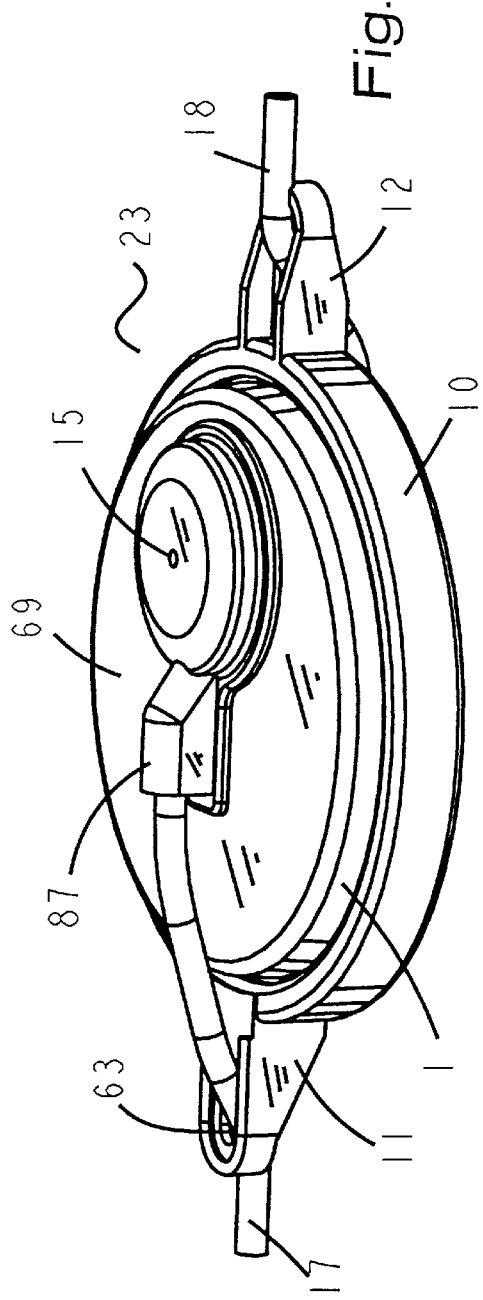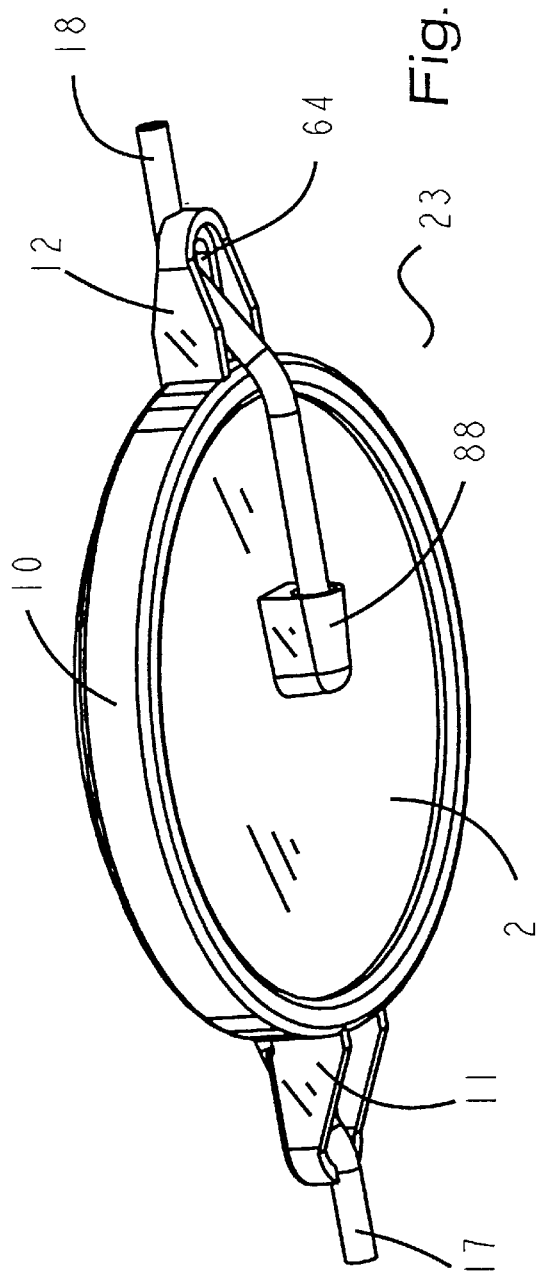

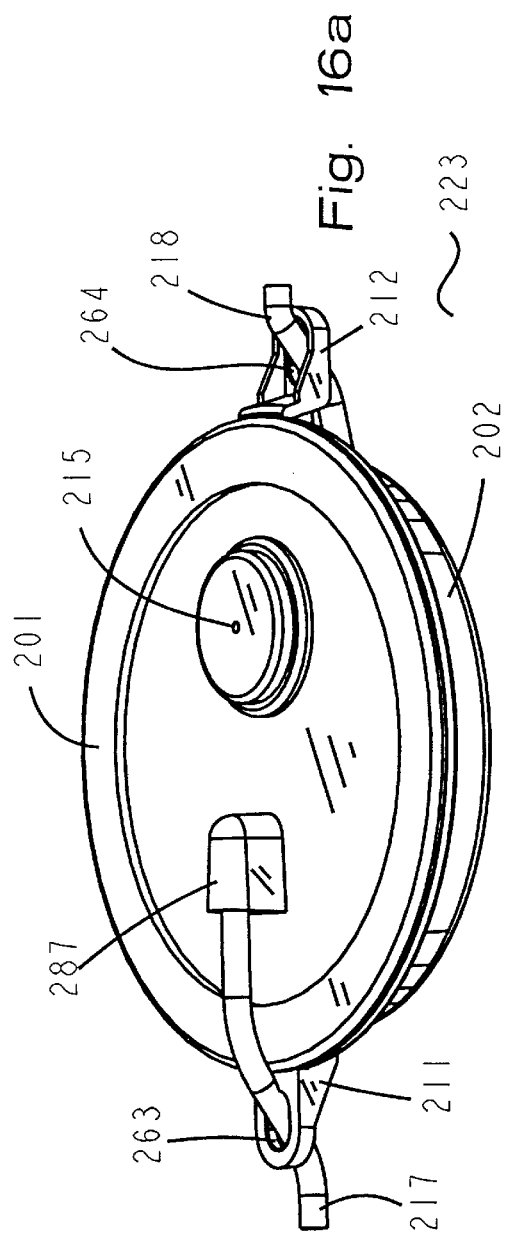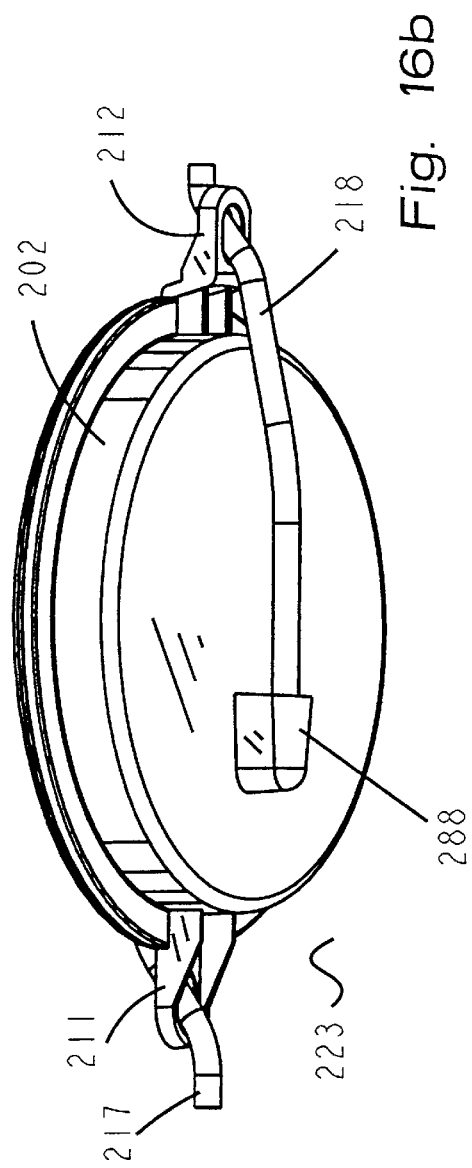

METHOD OF PREVENTING AIR FROM BECOMING ENTRAPPED WITHIN A FILTRATION DEVICE

FIELD OF INVENTION

This invention relates generally to liquid filtration devices. More particularly, this invention relates to an in-line gravity driven liquid filtration device usable to filter blood, blood products, cells and to remove chemical agents used to disinfect or otherwise treat blood or blood products.

BACKGROUND OF THE INVENTION

Typically, gravity feed blood filtration devices require user manipulation of vent filters during the filtration process. The manipulation of the vent filters must occur at the proper time during the filtration process or the system will not filter properly and blood being filtered may be rendered unusable. Since user manipulation of vent filters is time consuming and costly, it is desirable to achieve a liquid filtration device which may filter blood without the manipulation of vent filters or filtration devices. Moreover, blood filtration devices usually allow liquid to remain within the filtration device after filtration has occurred. This remaining liquid, referred to as a hold up volume, is often greater than the desired maximum amount. Also, blood filtration devices allow an undesirably high amount of air that is purged therefrom to be left in the receiving blood bag.

The filtration device disclosed in U.S. Pat. No. 5,472,605, and entitled "A Filtration Device Usable for Removal of Leukocytes and Other Blood Components" issued Dec. 5, 1995, and the filtration device disclosed in U.S. Ser. No. 08/524,049, U.S. Pat. No. 5,798,041, and entitled "an In-Line Liquid Filtration Device Usable for Blood, Blood Products and the Like" filed Sep. 6, 1995, and the filtration device disclosed in U.S. Ser. No. 08/449,362, abandoned, and entitled "A Filtration Device Usable for Removal of Leukocytes and Other Blood Components" filed May 24, 1995, and the filtration device disclosed in U.S. Ser. No. 08/661,804, abandoned, and entitled "A Filtration Device Usable for Removal of Leukocytes and Other Blood Components" filed Jun. 11, 1996, which are hereby incorporated by reference and made a part of the disclosure herein, overcome the aforementioned vent filter manipulation problem. However it is desirable to further reduce the hold up volume of this device, and to allow the device to be used in a vertical orientation, and not drain the outlet tubing so that the blood left in the outlet tubing can be used for cross matching, and to further reduce the manufacturing cost thereof, while maintaining an acceptable total filtration time.

Furthermore, it is desirable to eliminate air pockets within the device. Air pockets will reduce the effective filtration system area by reducing the area of the filter elements where blood may flow.

Although blood filtration devices may provide a means to separate gas from liquid and then vent the gas from the device to atmosphere, they are usually not designed to automatically drain the liquid from the upstream side of the device once filtration has stopped. Moreover, blood filtration devices typically do not have features which prevent the tubing attached thereto from becoming kinked thus impeding blood flow. It is, therefore, desirable to achieve a liquid filtration device which filters blood without the manipulation of vent filters, minimizes hold up volume, that automatically drains the upstream side of the device when the filtration process is complete, that minimizes the volume of air that is added to the receiving blood bag, that reduces air pocket therein, that reduces the possibility of kinked tubing when the device is assembled into a filtration system and packaged for shipping, that can be used in a vertical orientation, and that does not drain the outlet tubing.

SUMMARY OF THE INVENTION

The shortcomings of the prior art may be alleviated and the aforementioned goals achieved by using a filtration device constructed in accordance with the principles of the present invention. The filtration device of the present invention is capable of filtering blood to remove leukocytes, other blood components, cells, and chemical agents which may be used to treat the blood.

The filtration device includes an outlet and inlet therein, a filtration media located within the outlet, and a first channel downstream of the filtration media in fluid flow relationship with the outlet and the filtration media. The cross sectional area of the first channel is defined, in part, by the distance between the filtration media and a surface of the filtration device. The cross sectional area is sized so that filtered biological liquid forces air in the first channel and through the outlet. The cross sectional area of the first channel should be less than or equal to the cross sectional area of the outlet.

The first channel may also be in fluid flow relationship with a second channel having a cross sectional area defined, in part, by the distance between the filtration media and a bottom of the second channel. The cross sectional area of the second channel may be sized so that filtered biological liquid forces air within the second channel to flow into the first channel and through the outlet. The second channel may be a circular shaped channel extending about the perimeter of the active area of the filtration media which intersects with the first channel at a single location. The cross sectional area of the second channel should be less than or equal to the cross sectional area of the first channel.

A plurality of parallel flow channels may be located so that filtered biological liquid therein flows into the first channel and through the outlet. The parallel flow channels have a cross sectional area defined, in part, by the distance between the filtration media and the bottom of the parallel flow channels. The cross sectional area of the parallel flow channel is sized to allow filtered liquid to force air therein to flow into the outlet. The space between each parallel channel should be greater than or equal to twice the width of the parallel flow channel. Also, the height of the parallel flow channels should be less than or equal to approximately twice the width of the channels.

A plurality of cross flow channels may intersect or flow between the parallel flow channels. The cross flow channels may have a cross sectional area defined, in part, by the distance between the filtration media and the bottom of the cross flow channels. The cross sectional areas of the cross flow channels are sized to allow filtered liquid therein to force air therein to flow into the parallel channels and into said outlet. The cross sectional area of the cross flow channels may be less than the cross sectional area of the parallel flow channels. The width of the cross flow channels should be approximately less than or equal to the width of the parallel flow channels. Also, the depth of the cross flow channels should be less than or equal to approximately half the depth of the parallel flow channels.

Air is prevented from becoming entrapped within the filtration device by flowing biological liquid through the filtration system and through the filtration device, creating a negative pressure downstream of filtration media within the filtration device, and forcing air within the filtration device downstream of the filtration media to flow through an outlet. The liquid is forced to flow at a flow rate sufficient to force air to flow into the outlet thereby preventing air from becoming trapped in the filtration media or downstream of the filtration media within the filtration device.

Air located downstream of said filtration device may be forced to flow into a flow path comprising a first channel leading to the outlet of the device using filtered biological liquid. Filtered biological liquid from a second channel may flow into the first channel at a flow rate sufficient to force air from therein into the first channel. Filtered biological liquid from parallel channels may flow into the second channel at a flow rate sufficient to force air from the parallel channels into the second channel. Moreover, filtered biological liquid from cross flow channels may flow into the parallel channels at a flow rate sufficient to force air therein into the parallel channels. Biological liquid may remain within a tube located downstream of said filtration media after filtration has ceased. The biological liquid may be filtered for the removal of cells or chemical agents. Moreover, the biological liquid may be blood or a blood product.

In another aspect of the invention, the filtration device includes a first chamber which contains an automatic vent filter which is capable of draining the upstream side of the filtration device when filtration is complete, a second chamber in fluid flow relationship with the first chamber and capable of collecting and directing the flow of unfiltered liquid therein, a flow restriction port that connects the first chamber to the second chamber and which restricts the flow of liquid, and a low hold up volume filter support structure in fluid flow relationship with the second chamber capable of collecting and directing the flow of filtered fluid.

In another aspect of the invention, the filtration device includes a first chamber which contains an automatic vent filter which is capable of draining the upstream side of the filtration device when filtration is complete, said first chamber also contains at least two restriction channels which prevent the restriction port from clogging, a second chamber in fluid flow relationship with the first chamber and capable of collecting and directing the flow of unfiltered liquid therein, a flow restriction port that connects the first chamber to the second chamber and which restricts the flow of liquid, and a low hold up volume filter support structure in fluid flow relationship with the second chamber capable of collecting and directing the flow of filtered fluid.

In yet another aspect of the invention, the filtration device includes a first chamber which contains an automatic vent filter which is capable of draining the upstream side of the filtration device when filtration is complete, a second chamber in fluid flow relationship with the first chamber and capable of collecting and directing the flow of unfiltered liquid therein, and a low hold up volume filter support structure in fluid flow relationship with the second chamber capable of collecting and directing the flow of filtered fluid.

BRIEF DESCRIPTION OF THE DRAWINGS

The invention may be best understood by reference to the detailed description of the preferred embodiments herein when read in conjunction with drawings in which:

FIG. 1 depicts an unassembled isometric view of the components that make up a filtration device incorporating an automatic vent filter assembly, positioned upstream of the of the filtration elements, with a flow restriction constructed in accordance with the principles of the present invention;

FIG. 2 depicts a sectional representation from the side of the filtration device of FIG. 1 and the flow of fluid therein in accordance with the principles of the present invention;

FIG. 3 depicts an isometric view of the inside surface of the outlet section of the filtration device depicted in FIG. 1 and FIG. 2 constructed in accordance with the principles of the present invention;

FIG. 4 depicts an isometric view of the inside surface of the inlet section of a filtration device, such as that depicted in FIG. 1 and FIG. 2, constructed in accordance with the principles of the present invention;

FIG. 5 depicts an isometric view of a vent insert of a filtration device, such as that depicted in FIG. 1 and FIG. 2, constructed in accordance with the principles of the present invention;

FIG. 6*a* depicts a top view of a vent insert having a large particle trap useable in the filtration device, such as that depicted in FIG. 1 and FIG. 2, constructed in accordance with the principles of the present invention;

FIG. 6*b* depicts a top isometric view of the vent insert of FIG. 6*a;*

FIG. 7*a* depicts a top isometric view of the assembled filtration device depicted in FIG. 1 and FIG. 2;

FIG. 7*b* depicts a bottom isometric view of the assembled filtration device depicted in FIG. 1 and FIG. 2;

FIG. 8 depicts the filtration device of FIG. 1 and FIG. 2 in an operational assembly with a blood supply bag, a blood receiving bag, and an air bag in accordance with the principles of the present invention;

FIG. 9 depicts a sectional representation from the side of a filtration device without a flow restriction depicting the flow of fluid therein constructed in accordance with the principles of the present invention;

FIG. 10 depicts the filtration device of FIG. 9 in an operational assembly with a blood supply bag, a blood receiving bag, and an air bag;

FIG. 11 depicts an unassembled isometric view of an alternate embodiment of a filtration device incorporating an upstream automatic vent filter assembly constructed in accordance with the principles of the present invention;

FIG. 12 depicts a sectional schematic representation of the filtration device of FIG. 11 depicting the flow of fluid therein;

FIG. 13 depicts an isometric view of the inside surface of the outlet section of a filtration device, such as that depicted in FIG. 11 and FIG. 12 in accordance with the principles of the present invention;

FIG. 14 depicts an isometric view of the inside surface of the inlet section of the filtration device depicted in FIGS. 11 and 12;

FIG. 15 depicts a top isometric view of a vent insert of a filtration device, such as that depicted in FIG. 11 and FIG. 12 and constructed in accordance with the principles of the present invention;

FIG. 16*a* depicts a isometric view from the top of the assembled filtration device depicted in FIG. 11 and FIG. 12;

FIG. 16*b* depicts a isometric view from the bottom of the assembled filtration device depicted in FIG. 11 and FIG. 12;

FIG. 17 depicts the filtration device of FIG. 11 and FIG. 12 in an operational assembly with a blood supply bag, a blood receiving bag, and an air bag useable in accordance with the principles of the present invention; and FIG. 18 depicts a detailed view of a portion of the inside surface of the outlet section of a filtration device, such as that depicted in FIG. 13, showing shallow cross channels between the vertical channels.

DETAILED DESCRIPTION OF THE PREFERRED EMBODIMENTS

As referred to herein, the terms upstream, top or up refers to a location of the flow of liquid prior to filtration through filter elements within the filtration device of the present invention. Conversely, the terms downstream, bottom or down as used herein refers to a location of the flow of liquid after filtration through filter elements within the filtration device of the present invention.

As disclosed herein, the filtration device of the present invention is preferably disc or cylindrical shaped and intended to be used for in-line gravity filtration. The filtration device of the present invention may be used for the filtration of various liquids including biological liquids. However, it is particularly suited for the filtration of blood and/or blood products and will be described herein in reference to blood filtration.

Although various embodiments of the filtration device constructed in accordance with the present invention are disclosed herein, each embodiment enables the filtration device to automatically drain the upstream side when filtration is complete. Draining occurs without the manipulation of various components, the use of in-line vent filters or other external means. The filtration device comprises a housing typically formed by an inlet section, an outlet section, one or more filter elements, and means for allowing gas to vent from the filtration device through an outlet port, and a means to automatically drain the upstream side of the filtration device once filtration is complete.

One embodiment of the filtration device, shown in FIG. 1, FIG. 2, FIG. 7a, and FIG. 7b and constructed in accordance with the principles of the present invention incorporates an automatic vent filter that contains a flow restriction. The filtration device may include an inlet section 1 an outlet section 2, filter elements 3, 4, 5, and 6, vent insert 7, hydrophobic filter 8, and hydrophobic filter 9. The inlet section 1 and outlet section 2 may be held together with over mold ring 10, that contains inlet tube hanging tab 11 and outlet tube hanging tab 12.

Figure 2:
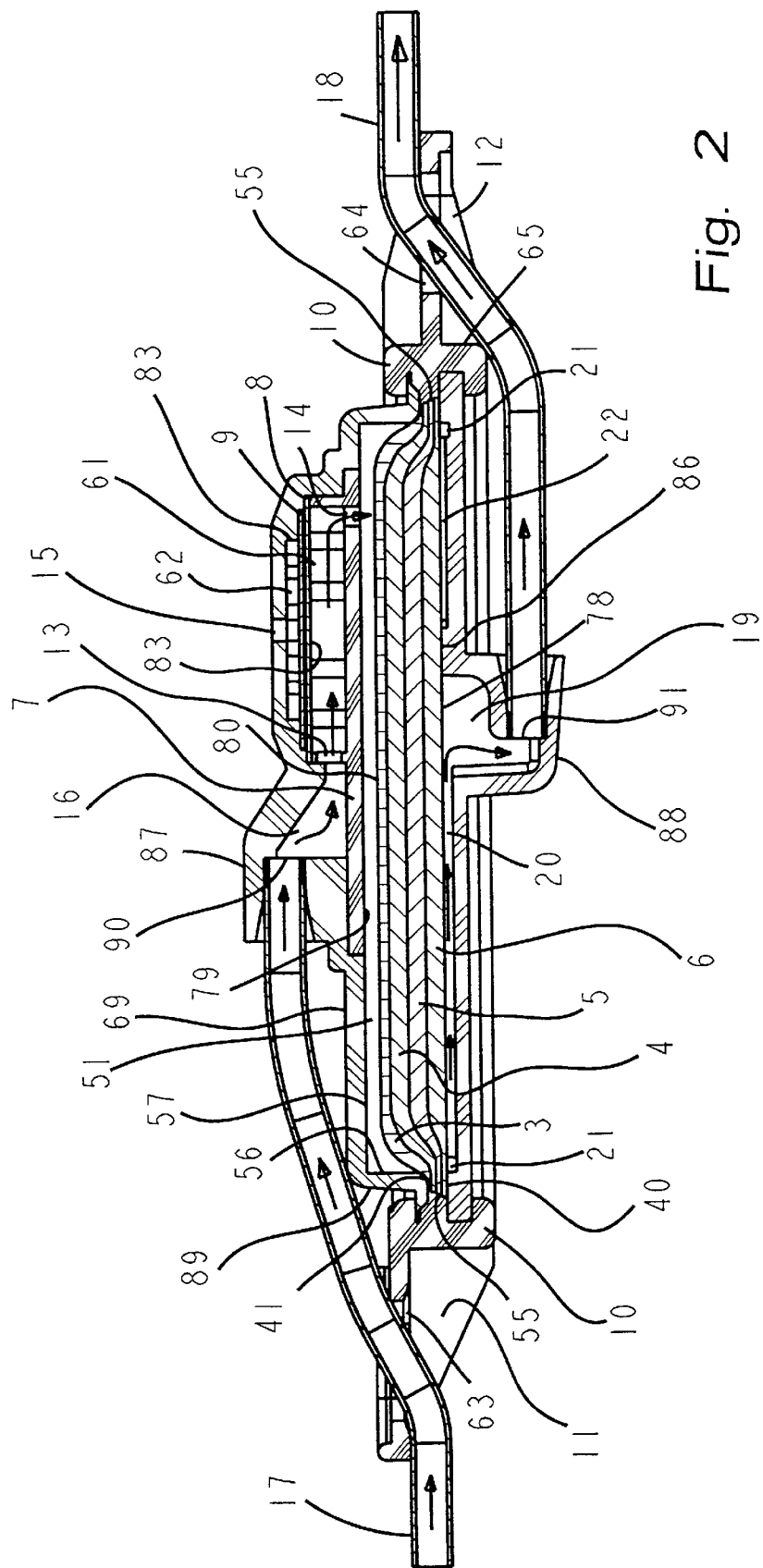
Figure 12:
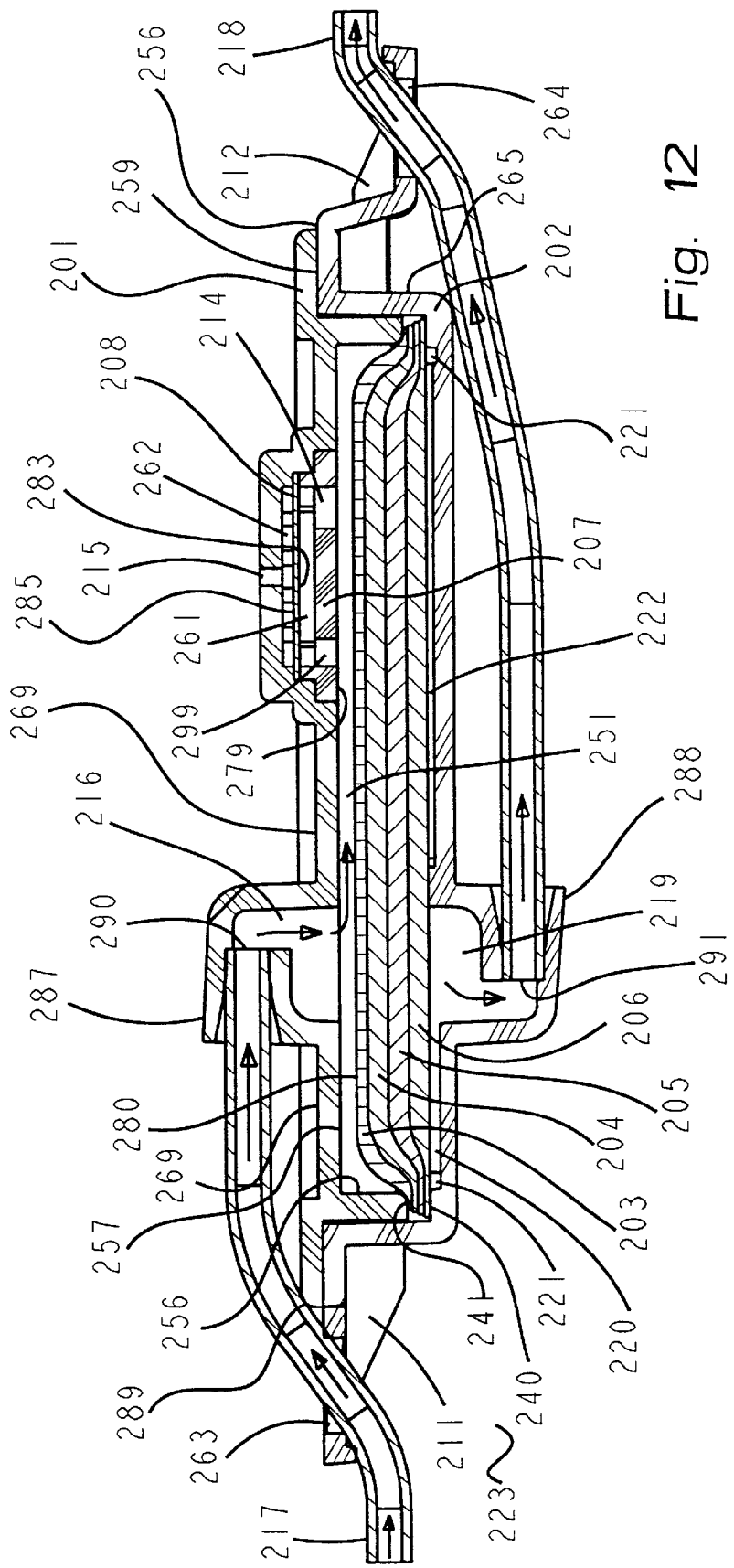

Referring to FIGS. 1 and 2 the filtration device 23 consists of inlet section 1 which is sealed to outlet section 2 by over mold ring 10. Inlet section 1 could however be sealed to outlet section 2 using, as illustrated in FIG. 12, an ultrasonic seal, a glue joint, a solvent bond, a heat bond, or any other type of seal. Filter elements 3, 4, 5, and 6 are sealed by the compression between surface 41 of inlet section 1 and surface 40 of outlet section 2. The molten plastic lip 55 which is a part of over mold ring 10, and which is forced up against the sides of filter elements 3, 4, 5, and 6 in the compression seal will enhance the quality of the compression seal. Filter elements 3, 4, 5, and 6 may all be of the same type, or filter element 3 may have a larger nominal pore size than filter elements 4, 5, and 6. When filter element 3 has a larger nominal pore size than filter elements 4, 5, and 6, filter element 3 will remove large particles from the blood prior to final filtration by filter elements 4, 5, and 6. Although the device illustrated in FIG. 1, FIG. 2, FIG. 7a, and FIG. 7b includes four filter elements, one or more filter elements of similar or different filtration characteristics may be used depending upon the liquid being filtered. For filtration of leukocytes from blood, conventional leukocytes filter elements may be used.

Referring to FIG. 2, within the interior of the filtration device is a cavity 16, cavity 19, cavity 51, cavity 61, and cavity 62. Referring again to FIG. 2, cavity 16 is in fluid flow relationship with the interior of inlet tubing 17 via port 90. Cavity 16 is also in fluid flow relationship with cavity 61 via port 13 of vent insert 7. Cavity 19 is in fluid flow relationship with the interior of outlet tubing 18 via port 91 of outlet section 2, and in fluid flow relationship with channel 20 of outlet section 2. Cavity 61 is in fluid flow relationship with cavity 51 via restriction port 14 of vent insert 7, and in fluid flow relationship to cavity 16 via port 13 of vent insert 7. Cavity 62 is in air flow relationship to atmosphere via port 15 and contains filter support ribs 45 and 46, as shown in FIG. 4, of inlet section 1.

Figure 3:
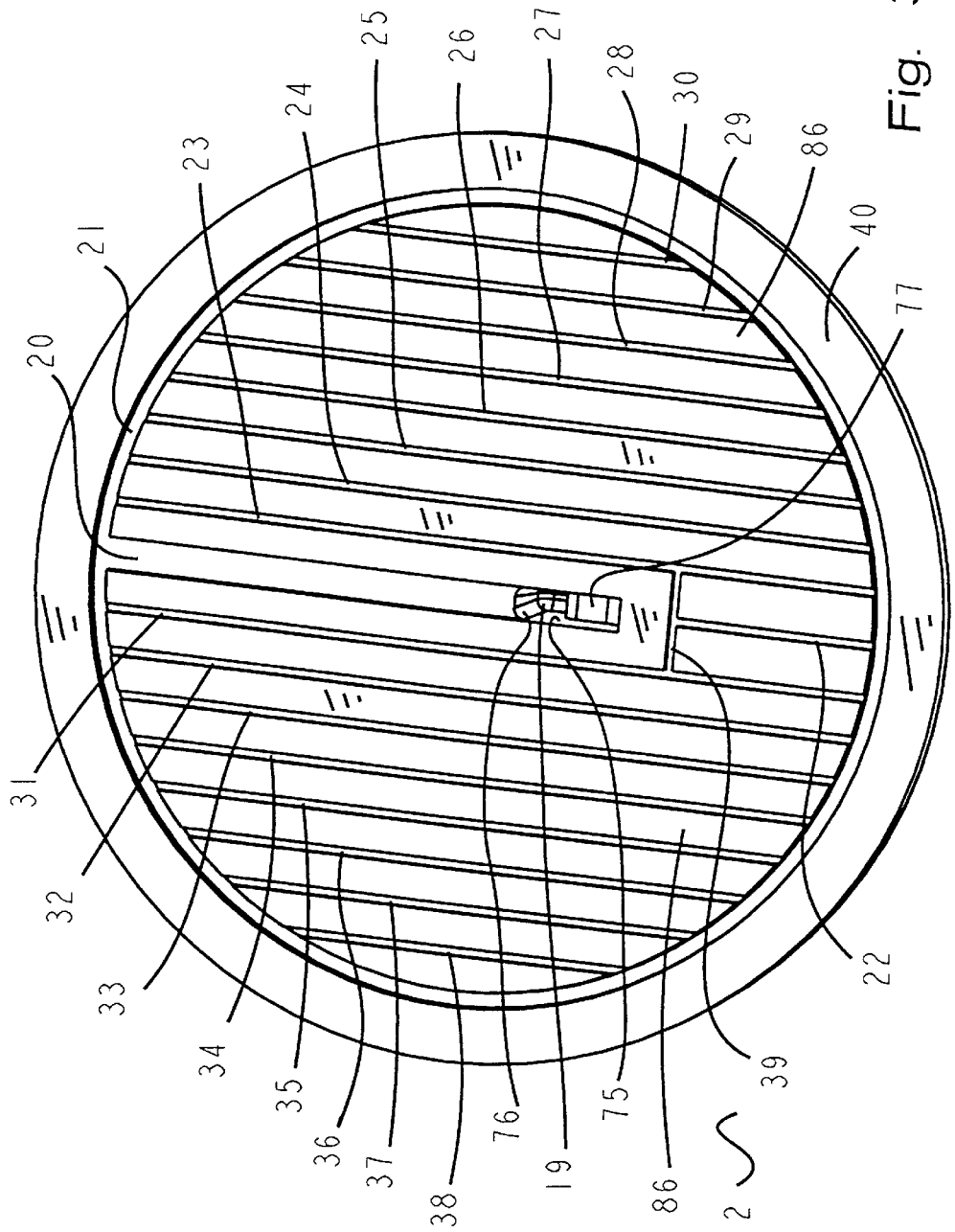
Figure 4:
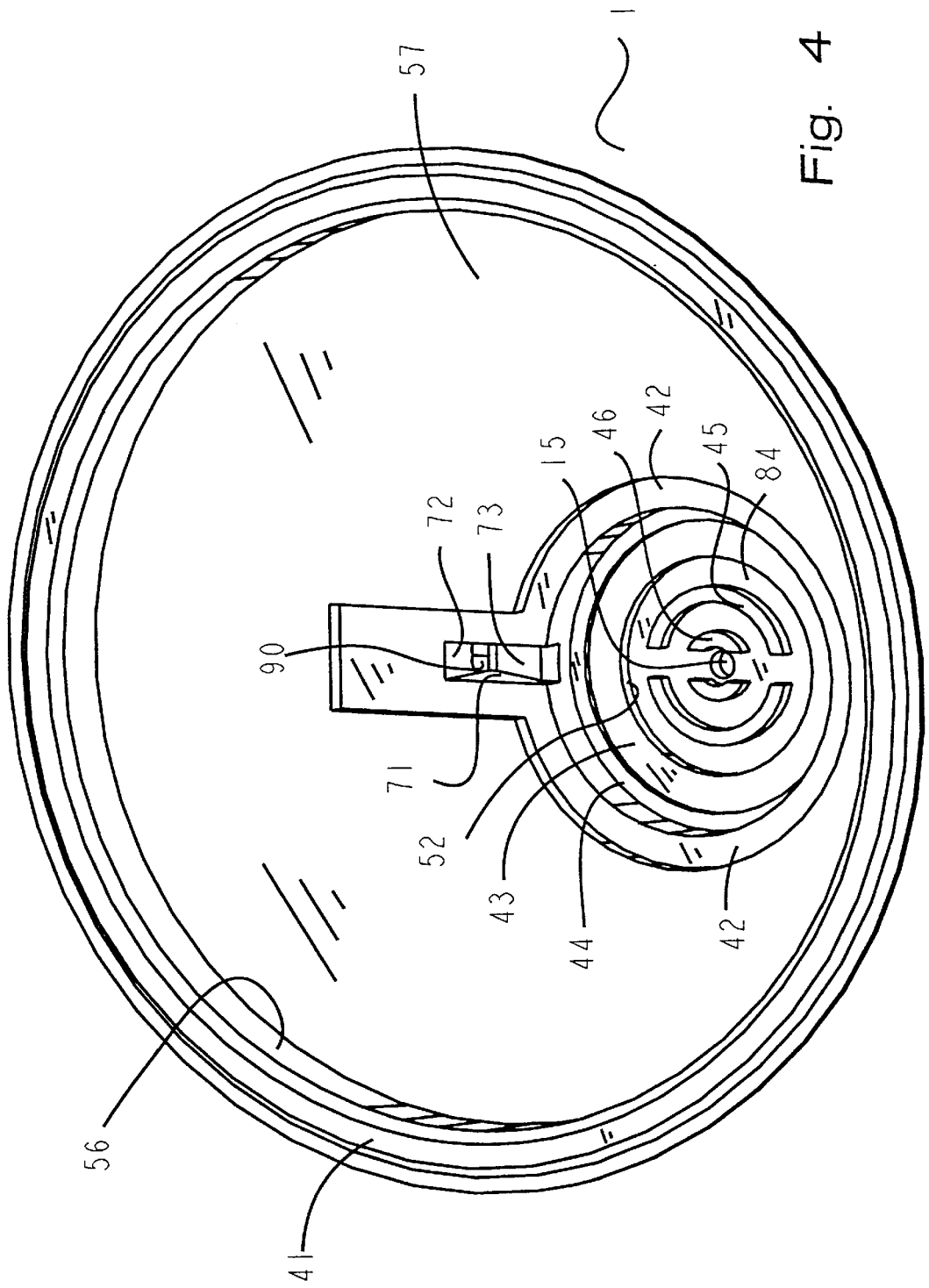

As shown in FIGS. 1, 4 and 5, cavity 16 is formed by the two side walls 71 of inlet section 1, wall 72 of inlet section 1, wall 73 of inlet section 1, and by wall 53 of vent insert 7. As shown in FIGS. 1, 2 and 3, cavity 19 is formed by the two side walls 75 of outlet section 2, wall 76 of outlet section 2, wall 77 of outlet section 2, and by the bottom surface 78 of filter element 6. As shown in FIG. 2, cavity 51 is formed by wall 56 of inlet section 1, wall 57 of inlet section 1, wall 79 of vent insert 7, and by top surface 80 of filter element 3. Also, cavity 62 is formed by wall 83 of inlet section 1, wall 52 of inlet section 1, and by top surface 85 of hydrophobic filter 9. As shown in FIGS. 2 and 5, cavity 61 is formed by wall 82 of vent insert 7, wall 81 of vent insert 7, and by bottom surface 83 of hydrophobic filter 8. Cavity 61 contains arcuately shaped filter support ribs 49 and 50 of vent insert 7.

Referring to FIGS. 1 through 5, and FIG. 7a, FIG. 7b, and FIG. 8, filtration device 23 may be assembled as follows.

First, referring to FIG. 1, disc shaped hydrophobic filter 9 may be sealed to complimentary shaped surface 43 located in a recessed area of inlet section 1. The seal is preferably a heat seal but could be a glue seal, a solvent seal, an ultrasonic seal, or any other seal that will make a leak tight bubble pointable seal. Once hydrophobic filter 9 is sealed to surface 43 of inlet section 1, cavity 62 (FIG. 2) will be formed. Disc shaped hydrophobic filter 9 may then be placed onto surface 44, also within the recessed area of inlet section 1, and may also be sealed thereto (FIG. 4). Surface 53 (FIG. 5) of vent insert 7 may then be sealed to surface 42 within the recessed section of inlet section 1. This seal is preferably an ultrasonic seal, but could be a glue seal, a heat seal, a solvent bond, or any other type of seal that will form a leak tight seal. Vent insert 7 is shaped to fit within the recessed area of inlet section 1 and contains a plurality of ribs 48, 49, 50 protruding from its inside surface as well as restriction port 14 therein. Once vent insert 7 is sealed to inlet section 1, hydrophobic filter 9 will be compressed and, therefore, sealed between surface 44 of inlet section 1 and surface 92 of rib 48 of vent insert 7. Once vent insert 7 and hydrophobic filter 9 are sealed in place cavity 61 (FIG. 2) will be formed.

Referring still to FIG. 1, filter elements 3, 4, 5, and 6 may then be placed onto inside surface 40 of outlet section 2, and onto inside surface 86 of outlet section 2. Surface 40 of outlet section 2 and surface 86 of outlet section 2 lie in the same plane. The sub assembly made up of inlet section 1, hydrophobic filter 8, hydrophobic filter 9, and vent insert 7 may now be placed onto filter element 3 so that the surface of lip 41 of inlet section 1 contacts the outer periphery of the top of filter element 3. The entire assembly may then be placed into a mold. When the mold closes inlet section 1 will be pushed down relative to outlet section 2, thus creating the compression seal of filter elements 3, 4, 5, and 6. While the mold is in the closed position over mold ring 10 along with inlet tube hanging tab 11, and outlet tube hanging tab 12 may then be molded in place. The completed filtration device 23 may now be removed from the mold.

Referring to FIGS. 2 and 7a, inlet section 1 contains tube socket 87. The outlet end of inlet tubing 17 fits within and is bonded to tube socket 87 of inlet section 1. Tube socket 87 of inlet section 1 should be positioned far enough away from the top end 89 of inlet section 1 so that when the inlet tubing 17 is placed through the opening 63 in inlet tube hanging tab 11, the section of inlet tubing 17 between tube socket 87 of inlet section 1 and the opening 63 in inlet tube hanging tab 11 will not kink. Inlet tube hanging tab 11 also allows inlet tubing 17 to be coiled for shipping without kinking.

Referring to FIGS. 2 and 7b, outlet section 2 contains tube socket 88. The inlet end of outlet tubing 18 fits within and is bonded to tube socket 88 of outlet section 2. Tube socket 88 of outlet section 2 should be positioned far enough away from the bottom end 65 of over mold ring 10 so that when the outlet tubing 18 is placed through the opening 64 in outlet tube hanging tab 12 the section of outlet tubing 18 between tube socket 88 of outlet section 2 and the opening 64 in outlet tube hanging tab 12 will not kink. Outlet tube hanging tab 12 also allows outlet tubing 18 along with receiving blood bag 94 and air bag 95 to be coiled for shipping without kinking outlet tubing 18.

Referring to FIG. 3, outlet section 2 also contains channels 22–39, which are narrow and shallow, and in fluid flow relationship with channel 21 which has a cross sectional area large enough to accommodate the combined flow from channels 22 through 39. Channel 21 is in fluid flow relationship with channel 20, which is in turn in fluid flow relationship with cavity 19, which is in fluid flow relationship with the interior of outlet tubing 18 through port 91 (FIG. 2). Channel 20 has a cross sectional area large enough to accommodate the flow from both sides of channel 21 so that as much of the filtered blood as possible is recovered in a receiving blood bag. To minimize blood hold up in the filter support and drain structure that is made up of channels 20 through 39, the space between channels (for channels 22 through 38) is much greater than the width of the channels. The ratio of distance between channels to channel width is dependent on the structure of filter element 6. Preferably the filter element 6 (FIG. 2) has an open structure, so that the distance between channels may be greater than four times the width of the channels. The bottom of filter element 6 contacts surface 86 of outlet section 2 and surface 40 of outlet section 2. However, since surfaces 86 and 40 are coplanar, the bottom surface of filter element 6 closes off the top of channels 20 through 39. Hence channels 20 through 39 effectively become segments of tubing with the top face of each tube being porous.

The device may have one or more drain channels that split into multiple channels. An example of this design is illustrated in FIG. 3. The drain channel 20 empties into the outlet port and is fed from the right and from the left by channel 21. As used herein, "parallel flow channels" refers to one or more channels which feed into a downstream channel so that liquid or air in any one of a multiple of parallel flow channels will be forced to flow eventually downstream into a common downstream channel. Parallel flow channels 22–38 feed into channel 21. For optimum performance, the cross sectional area of the drain channel 20 should not exceed the cross sectional area of the outlet or outlet tubing. The portions of channel 21 that connect with the drain channel 20 should be smaller in cross section than the drain channel 21 and not wider than the width of the drain channel 20. The portions of channel 21 which intersect with channel 20 should be small enough in cross section to ensure that the velocity of liquid flowing through them is sufficiently great to force any air that enters them into channel 20 especially after they are filled with liquid. Likewise, parallel flow channels 22–39 should be small enough in cross section to ensure that the velocity of liquid flowing through them is sufficiently great to force any air that enters them, especially after they are filled with liquid, to flow into channel 20 and eventually through outlet. The space or distance between parallel flow channels 22–39 should be greater than or equal to twice the width of the parallel flow channels to ensure proper liquid flow velocity to force air out of the device. Also, the height of the parallel flow channels should be less than or equal to twice the width of these channels.

Figure 8:
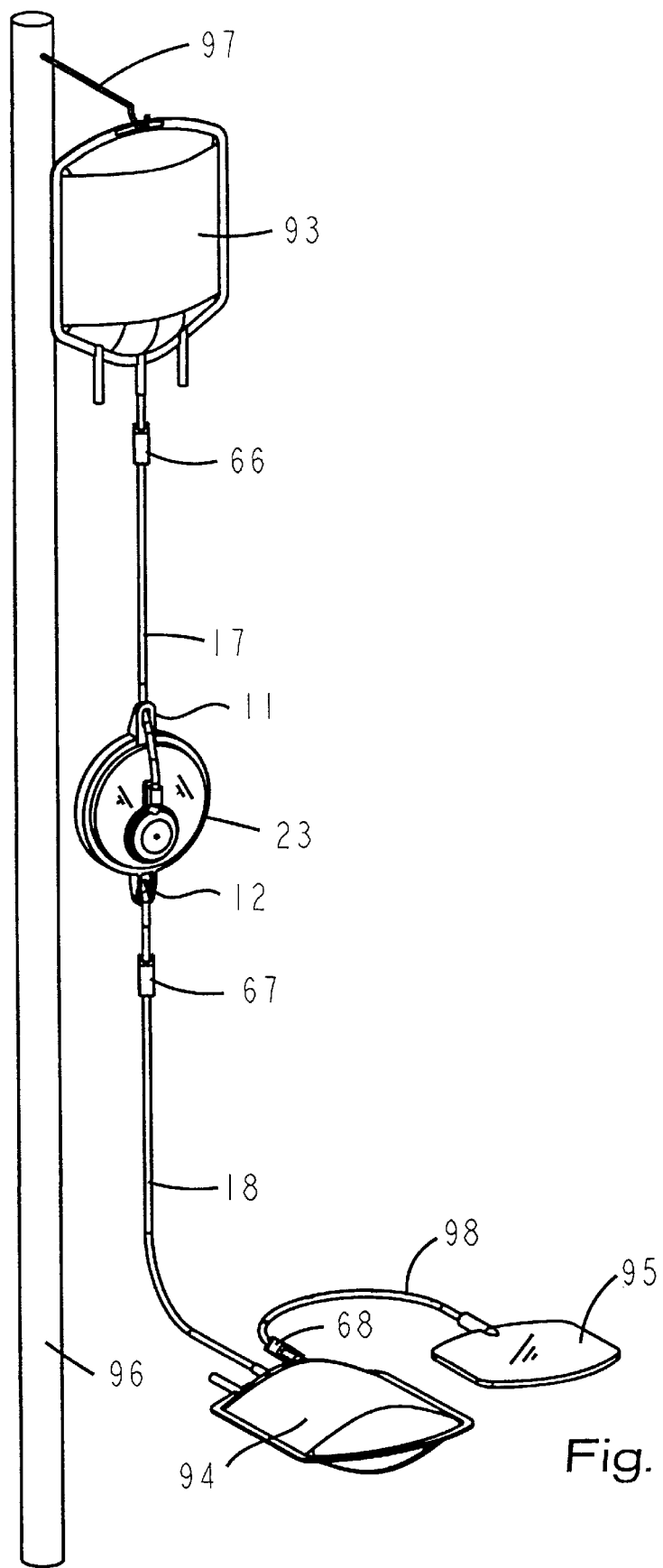

Referring to FIG. 8, the filtration device 23 is in an operational assembly with inlet tubing 17, outlet tubing 18, feed blood bag 93, receiving blood bag 94, air bag 95, inlet tube clamp 66, outlet tube clamp 67, and air tube clamp 68. Preferably, the user will purchase the assembly of FIG. 8 sterilized without feed blood bag 93 with the inlet end of inlet tubing 17 sealed to maintain system sterility. For performing filtration the user may first close inlet tube clamp 66 close to the inlet end of inlet tubing 17. Next the user should open outlet tube clamp 67 and close air tube clamp 68 (close to the air tube port on receiving blood bag 94). Inlet tubing 17, attached to tube socket 87 above the center of inlet section 1, is now connected to feed blood bag 93 using a sterile docking device as is well known in the art. Once the sterile docking connection is made the user will hang feed blood bag 93 from hook 97 on blood bag pole 96. Receiving blood bag 94 and air bag 95 should be placed on a surface such as a table top or the like. The complete assembly ready for filtration is illustrated in FIG. 8. When the filtration device 23 is in operational assembly as illustrated in FIG. 8, the inlet tube hanging tab 11 and outlet tube hanging tab 12, position inlet tubing 17 and outlet tubing 18 respectively so that filtration device 23 hangs vertical and plumb as illustrated in FIG. 8.

Referring to FIG. 2 and FIG. 8 the filtration is performed as follows. The user opens inlet tube clamp 66. Gravity now forces blood to flow from feed blood bag 93, through inlet tubing 17, through port 90 of inlet section 1, through cavity 16, through port 13 of vent insert 7, through cavity 61, through restriction port 14 of vent insert 7, into cavity 51 above the bottom of cavity 51. Air in inlet tubing 17 and cavity 16 and air that was in cavity 61 before blood flow started will be pushed ahead of the blood, and forced through restriction port 14 into cavity 51. Once blood starts to fill cavity 61, restriction port 14 will cause blood to back up in cavity 61 and fill cavity 61. Once cavity 61 is filled with blood there will be a positive pressure in cavity 61. This positive pressure will prevent air from entering cavity 61 via port 15 of inlet section 1, and hydrophobic filters 8 and 9. The vent assembly that is made up of cavity 61, hydrophobic filter 9, hydrophobic filter 8, cavity 62, port 15, and restriction port 14 can be located any where on face 69 of inlet section 1. Hydrophobic filter 9 must be bacteria retentive. Hydrophobic filter 8 should be of a much larger pore size than hydrophobic filter 9 to prevent hydrophobic filter 9 from fouling with blood. The purpose of the vent assembly is to let air into the device when filtration is complete to drain the upstream side of the device, not to vent air out of the device. Therefore, there is little restriction on the volume of cavity 61.

Referring still to FIGS. 2 and 8, as cavity 51 of inlet section 1 fills from the bottom up, the air in cavity 51 will be forced through filter elements 3, 4, 5, and 6. This initial air will flow into channels 20 through 39 and then flow through cavity 19 (FIG. 3), through port 91, into outlet tubing 18, into receiving blood bag 94. Filter elements 3, 4, 5, and 6 will also wet from the bottom up. The air that is initially in filter elements 3, 4, 5, and 6 will be displaced by blood and flow into channels 20 through 39 and then flow through cavity 19, through port 91, into outlet tubing 18, into receiving blood bag 94. Because the volume of cavity 51 is small, and the flow rate of blood entering cavity 51 from port 14 of vent insert 7 is much greater than the initial flow rate of blood through filter elements 3, 4, 5, and 6, cavity 51 will fill before filter elements 3, 4, 5, and 6 become wet with blood. Also, the pressure head at the bottom of cavity 51 will be larger than the pressure head at the top of cavity 51, because of the height difference between the top and bottom of cavity 51. Therefore blood will start to pass through filter element 6 from the bottom up. As the blood starts to pass through filter element 6 from the bottom up, the channels in outlet section 2 will fill from the bottom up. Because the total volume of the channels in outlet section 2 is small (to minimize holdup) the channels may fill with blood (from the bottom up) before the upper part of filter element 6 has wet with blood. Once blood starts to flow from channel 20 of outlet section 2, into cavity 19 of outlet section 2, through port 91 of outlet section 2, into outlet tubing 18, and starts to flow down outlet tubing 18 toward receiving blood bag 94, the pressure in cavity 19 will become negative. Because channel 20 is in fluid flow relationship with cavity 19, the pressure inside the tube created by channel 20 and the bottom surface of filter element 6 will also be negative. Likewise since channel 21 is in fluid flow relationship with channel 20 the pressure within channel 21 and will also be negative. Since the tube segments made up of channels 22 through 39 are also in fluid flow relationship with channel 21, any air or liquid that flows from filter element 6 into channels 22 through 39 will be sucked into channel 21, and then flow from channel 21 into channel 20, into cavity 19, through port 91, into outlet tubing 18, and into receiving blood bag 94. This assures that filter elements 3, 4, 5, and 6 will completely wet, and that all of the air that was in cavity 51, filter elements 3, 4, 5, and 6, channels 20 through 39, cavity 19, and the interior of outlet tubing 18 will be forced into receiving blood bag 94. Referring to FIG. 3, although channels 22 through 38 are shown in the vertical orientation, they could be orientated at any angle from zero degrees to ninety degrees from vertical, as long as they are in fluid flow relationship with channel 21. Other channel designs such as the spiral channel filter underdrain disclosed in U.S. Ser. No. 08/524,049, now U.S. Pat. No. 5,798,041, and entitled "An In-Line Liquid Filtration Device Usable for Blood, Blood Products and the Like", the specification of which is incorporated herein by reference, could also be used. However, all channels should be either directly or indirectly in fluid flow relationship with cavity 19.

To insure optimum performance the cross sectional area of a single continuous channel, or the sum of the cross sectional areas of parallel continuous channels leading to a single outlet port should not exceed the cross sectional area of the outlet port and outlet tubing. For equal length multiple continuous channels the cross sectional area of each channel should be equal for optimum performance. In a pattern containing unequal length continuous channels it may be desirable to make the cross sectional area of a short channel smaller than the cross sectional area of a long channel.

Blood filtration will continue until feed blood bag 93 is empty. When feed blood bag 93 is empty it will be collapsed and therefore close the inlet end of inlet tubing 17. Because outlet tubing 18 will be full of blood, and because the outside of receiving blood bag 94 is at atmospheric pressure, the pressure head in cavity 19 will be negative, as will be the pressure head in channels 20 through 39 of outlet section 2. Once blood flow has stopped the pressure drop across filter elements 3, 4, 5, and 6 will fall to zero. Hence the pressure in cavity 51 and cavity 61 will become negative. Once the pressure in cavity 61 falls below atmospheric pressure air will begin to flow from atmosphere into port 15, through sterilizing grade hydrophobic filter 9, through non sterilizing grade hydrophobic filter 8, into cavity 61. The sterile air that enters cavity 61 from port 15 will bubble up to the top of cavity 61, displacing the blood in cavity 61, thus causing cavity 61 to drain from the top down. Once cavity 61 has drained the negative pressure in cavity 51 will suck air from port 15, through sterilizing grade hydrophobic filter 9, through non sterilizing grade hydrophobic filter 8, into cavity 61, through restriction port 14 of vent insert 7, into cavity 51. The air will bubble up to the top of cavity 51, thus causing cavity 51 to drain from the top down. Because the air entering cavity 51 from port 14 bubbles to the top of cavity 51, thus draining cavity 51 from the top down, the sub assembly consisting of tube socket 87, cavity 16, port 13, cavity 61, cavity 62, port 15, and port 14, can be located anywhere on face 69 of inlet section 1. Filter elements 3, 4, 5, and 6 may be plugged sufficiently at this point, therefore very little if any blood may be sucked from these filter elements by the negative pressure in channels 20 through 39. Hence blood flow will stop after cavity 51 has drained and blood will remain in filter elements 3, 4, 5, and 6, and in channels 20 through 39 of outlet section 2, and in cavity 19 of outlet section 2, and in outlet tubing 18.

Referring now to FIG. 8, the user can now close tube clamp 67 on outlet tubing 18 and then seal tubing 18 above tube clamp 67, and then cut outlet tubing 18 above the seal just made. Feed blood bag 93, inlet tubing 17, and filtration device 23 can now be discarded in a safe manner. The user may now mix the blood in receiving blood bag 94, and then open tube clamp 68, and then express the air in receiving blood bag 94 through air bag tubing 98 into air bag 95. Once the air in receiving blood bag 94 has been expressed from receiving blood bag 94, the user may express enough of the blood from receiving blood bag 94 to fill air bag tubing 98. The user will now close tube clamp 68 and then seal air bag tubing 98 near the air bag. Air bag 95 may now be cut away above the seal just made and discarded in a safe manner. Both outlet tubing 18 and air bag tubing 98 may have segment marks thereon. The user may now seal the tubing in segments. The blood that is left in outlet tubing 18 may be used for cross matching, and the mixed blood in air bag tubing 98 may be used for quality control purposes.

Figure 6B:
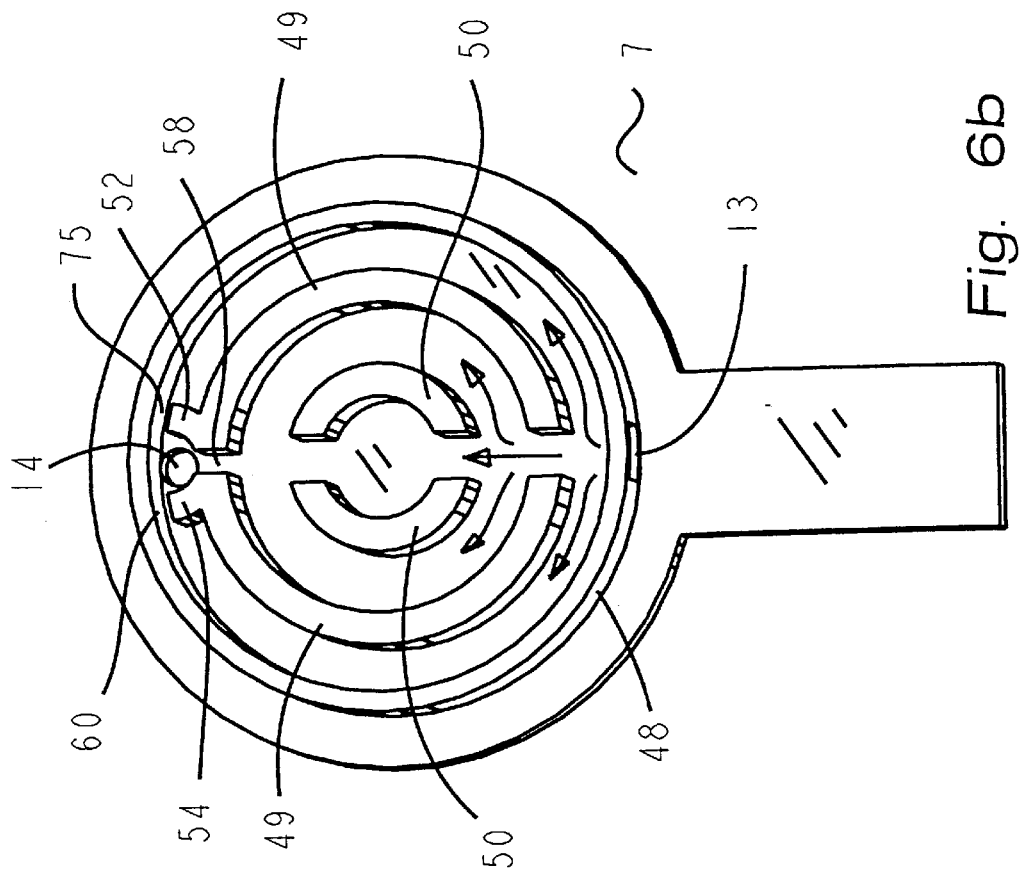
Figure 6A:
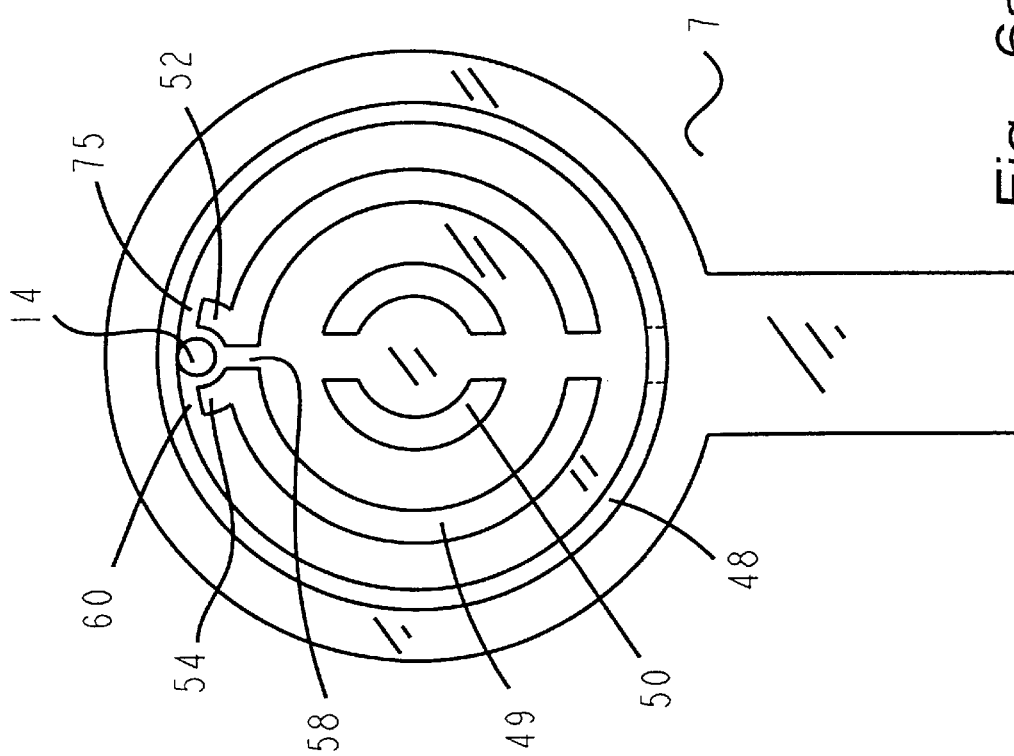

Referring to FIG. 6a and 6b an alternative embodiment of a vent insert 7 for use in the filtration device constructed in accordance with the principals of the present invention is shown. The vent insert 7 includes restriction channels 58, 60, and 75 formed between ribs 48, 49, 50 which protrude from the surface of the vent insert. The width of restriction channels 58, 60, and 75 should be less than the diameter of restriction port 14. In addition, the height of ribs 48, and 50, should be less than the diameter of restriction port 14. All blood that flows through port 14 must first flow through either restriction channel 58, restriction channel 60 or restriction channel 75. If the width and height of restriction channels 58, 60, and 75 is smaller than the diameter of restriction port 14, any large particles or clots may be trapped by either restriction channel 58, restriction channel 60, or restriction channel 75 before they can reach restriction port 14. Because restriction channels 58, 60, and 75 are in parallel with each other, filtration may continue as long as at least one of the restriction channels remains unclogged. The restriction channels may allow filtration device 23 to filter blood that may otherwise clog restriction port 14 and thus stop the filtration process before all the blood has been filtered. Although the vent insert illustrated in FIG. 6a and FIG. 6b contains three restriction channels, two or more restriction channels may be used.

Figure 9:
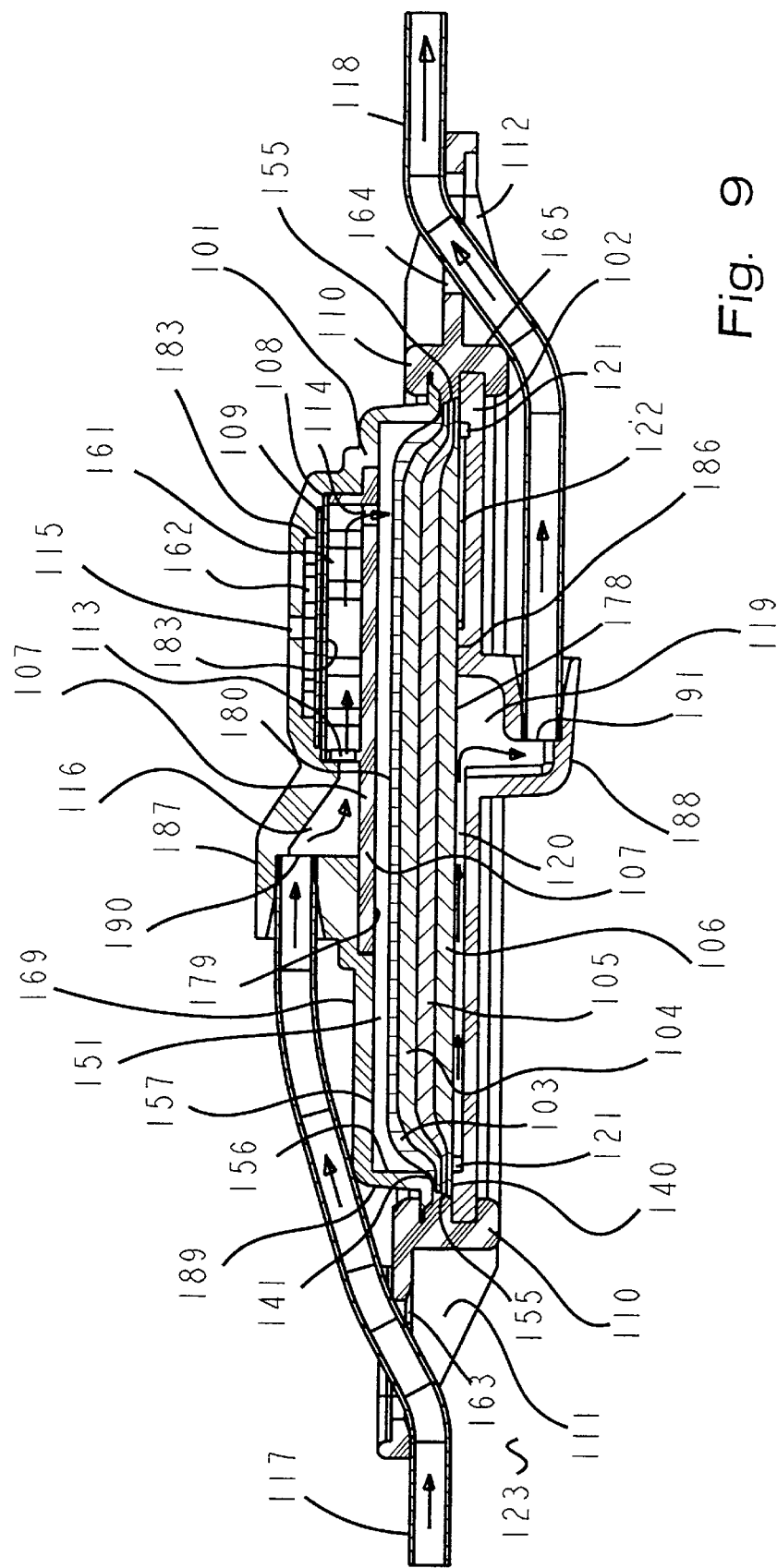

In an alternative embodiment of the filtration device 23, depicted in FIG. 9, port 114 of vent insert 107 is made large enough so it does restrict blood flow and therefore does not cause blood to back up in cavity 61. However, in this embodiment, filter elements 103, 104, 105, and 106 create enough of back pressure to the initial flow of blood to cause blood to back up in cavity 161 and restrict fluid flow.

Figure 10:
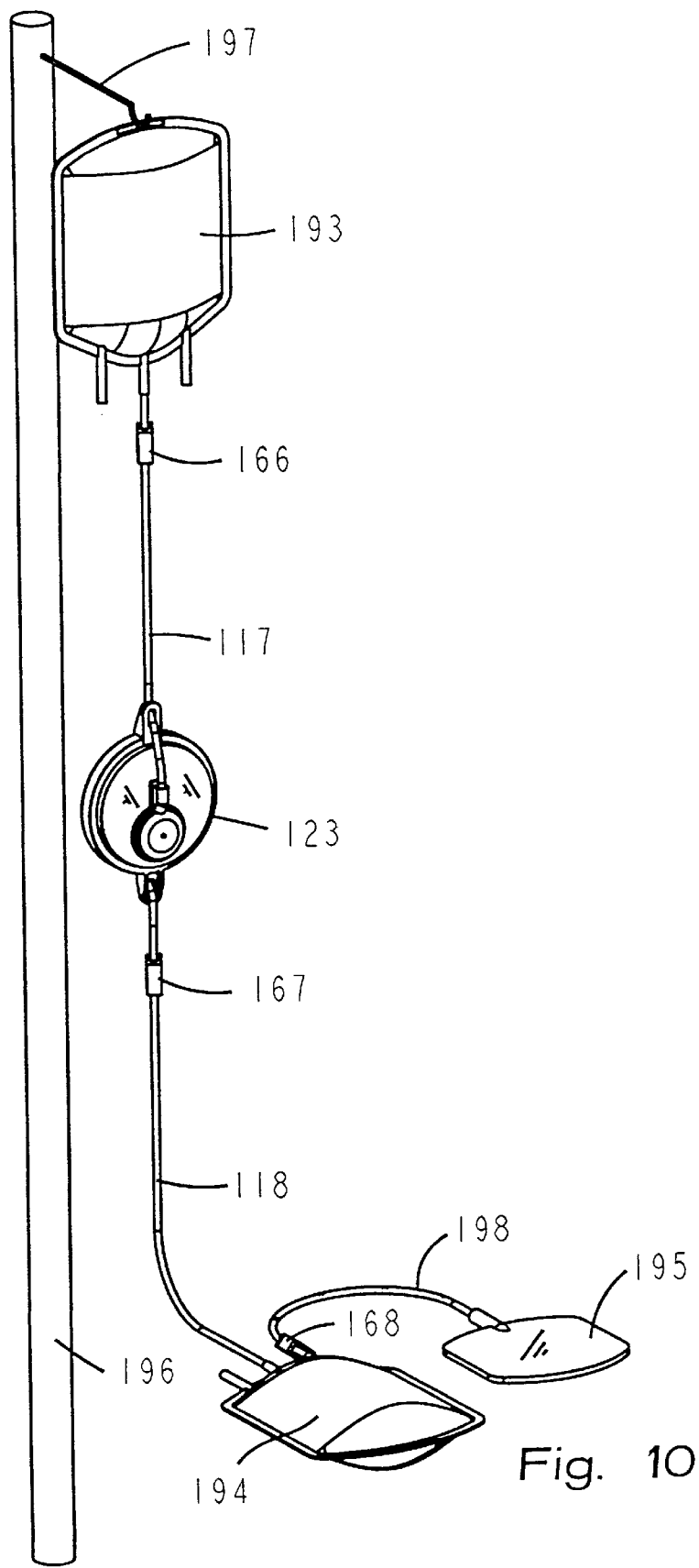
Figure 11:
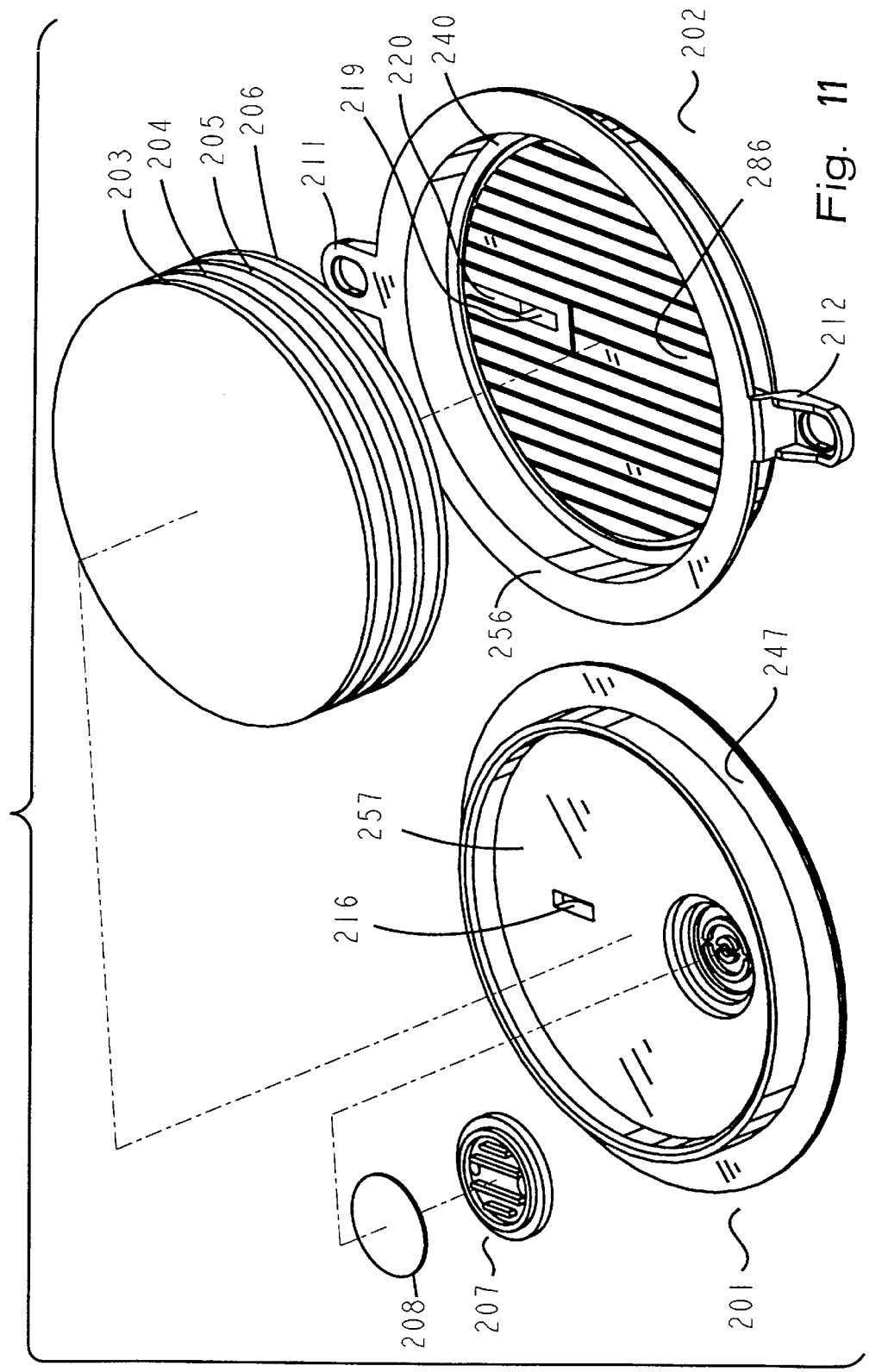

Referring to FIG. 9 and FIG. 10, the filtration is performed with this alternative embodiment as follows. The user opens inlet tube clamp 166. Gravity now forces blood to flow from feed blood bag 193, through inlet tubing 117, through port 190 of inlet section 101, through cavity 116, through port 113 of vent insert 107, through cavity 161, through non restriction port 114 of vent insert 107, into cavity 151 above the bottom of cavity 151. Air that was in inlet tubing 117 and cavity 116 and air that was in cavity 161 before blood flow started will be pushed ahead of the blood into cavity 151. Blood will flow through cavity 161 without filling cavity 161, and then flow out of cavity 161 through non restriction port 114 into cavity 151 above the bottom of cavity 151. Cavity 151 will fill from the bottom up. Once the level of blood in cavity 151 reaches non restriction port 114 of vent insert 107 blood will start to back up in cavity 161. The blood level will rise in cavity 161 at the same rate as the blood level rises in cavity 151. Once cavity 161 is filled with blood there will be a positive pressure in cavity 161. This positive pressure will prevent air from entering cavity 161 via port 115 of inlet section 101, and hydrophobic filters 109 and 108. The vent assembly that is made up of cavity 161, hydrophobic filter 108, hydrophobic filter 109, cavity 162, port 115, and non restriction port 114 can be located any where on face 169 of inlet section 101. Hydrophobic filter 109 must be bacteria retentive. Hydrophobic filter 108 should be of a much larger pore size than hydrophobic filter 109 to prevent hydrophobic filter 109 from fouling with blood. The purpose of the vent assembly is to let air into the device when filtration is complete, and thus drain the upstream side of the device, not to vent air out of the device. Therefore, the volume of cavity 161 is not critical. However, it is desirable to make the height of cavity 161, and the cross sectional area of ports 113 and 114 of vent insert 107, large enough so that any blood clot that may flow into device 123 from feed blood bag 193, will not stop the flow of blood before the filtration is complete. Once cavity 151 fills with blood the remainder of the filtration process is the same as previously described with filtration device 23.

A third embodiment of the filtration device, shown in FIG. 11, FIG. 12, FIG. 16a, and FIG. 16b also incorporates an automatic vent filter that does not contain a flow restriction. Referring to FIG. 12, the filtration device includes an inlet section 201 an outlet section 202, filter elements 203, 204, 205, 206, vent insert 207, and hydrophobic filter 208. Inlet section 201 is bonded to outlet section 202 at joint 259, preferably using ultrasonics. Joint 259 could however be a glue joint, a solvent bond, a heat bond, or any other type of bond that creates a leak tight seal.

Referring to FIG. 12, the filtration device 223 consists of inlet section 201 which is sealed to outlet section 202. Filter elements 203, 204, 205, and 206 are sealed by the compression seal between surface 241 of inlet section 201 and surface 240 of outlet section 202. Although four filter elements are shown, one or more filter elements may be used depending upon the type of liquid being filtered and the type of filter elements used.

The interior of device 223 contains cavity 216, cavity 219, cavity 251, and cavity 261. Cavity 216 is similar to cavity 16 of the device depicted in FIGS. 1, 2, and 4. cavity 216 is in fluid flow relationship with the interior of inlet tubing 217 via port 290. Cavity 216 is also in fluid flow relationship with cavity 251. cavity 219 is similar to cavity 19 of the device depicted in FIGS. 1, 2, and 3. Cavity 219 is in fluid flow relationship with the interior of outlet tubing 218 via port 291 of outlet section 202. Cavity 219 is also in fluid flow relationship with channel 220 of outlet section 202. Cavity 251 is in fluid flow relationship with cavity 261 via port 214 of vent insert 207, and via port 299 of vent insert 207. Cavity 262 is in air flow relationship to atmosphere via port 215. Cavity 262 contains filter support ribs 245 and 246 of inlet section 201. Cavity 251 is formed by wall 256 of inlet section 201, wall 257 of inlet section 201, wall 279 of vent insert 207, and by top surface 280 of filter element 203. Cavity 261 is formed by wall 282 of vent insert 207, wall 281 of vent insert 207, and by bottom surface 283 of hydrophobic filter 208. Cavity 261 contains elongate linear shaped filter support ribs 249, 250, 270, and 274 of vent insert 207. Cavity 262 is formed by wall 283 of inlet section 201, wall 284 of inlet section 201, and by top surface 285 of hydrophobic filter 208.

Referring to FIGS. 11 through 17, filtration device 223 may be assembled as follows. First, referring to FIG. 11, sterilizing grade hydrophobic filter 208 may be sealed to surface 243 of inlet section 201. The seal is preferably a heat seal but could be a glue seal, a solvent seal, an ultrasonic seal, or any other seal that will make a leak tight bubble pointable seal. Once hydrophobic filter 208 is sealed to surface 243 of inlet section 201, cavity 262 (FIG. 12) will be formed. Surface 253 (FIG. 15) of vent insert 207 may now be sealed to surface 242 of inlet section 201. This seal is preferably also an ultrasonic seal, but could be a glue seal, a heat seal, a solvent bond, or any other type of seal that will form a leak tight seal. Once vent insert 7 is sealed in place cavity 261 (FIG. 12) will be formed. Filter elements 203, 204, 205, and 206 may now be placed onto surface 240 of outlet section 202, and onto surface 286 of outlet section 202. Surface 240 of outlet section 202 and surface 286 of outlet section 202 lie in the same plane. The sub assembly made up of inlet section 201, hydrophobic filter 208, and vent insert 207 may now be placed onto filter element 203 so that surface 241 of inlet section 201 contacts the outer periphery of the top of filter element 203. Inlet section 201 may now be pushed down preferably using ultrasonics until surface 247 of inlet section 201 is bonded to surface 256 of outlet section 202 to form joint 259 (FIG. 12). Once joint 259 is formed the outer periphery of filter elements 203, 204, 205, and 206 are sealed by compression between surface 241 of inlet section 201 and surface 240 of outlet section 202.

Referring to FIG. 16a, inlet section 201 contains tube socket 287. The outlet end of inlet tubing 217 is bonded to tube socket 287 of inlet section 201. Tube socket 287 of inlet section 201 should be positioned far enough away from the top edge 289 of inlet section 201 so that when the inlet tubing 217 is placed through the opening 263 in inlet tube hanging tab 211 the section of inlet tubing 217 between tube socket 287 of inlet section 201 and the opening 263 in inlet tube hanging tab 211 will not kink. Inlet tube hanging tab 211 also allows inlet tubing 217 to be coiled for shipping without kinking.

As shown in FIG. 16b, outlet section 202 contains tube socket 288. The inlet end of outlet tubing 218 is bonded to tube socket 288 of outlet section 202. Tube socket 288 of outlet section 202 should be positioned far enough away from the bottom end 265 of outlet section 202 so that when the outlet tubing 218 is placed through the opening 264 in outlet tube hanging tab 212 the section of outlet tubing 218 between tube socket 288 of outlet section 202 and the opening 264 in outlet tube hanging tab 212 will not kink. Outlet tube hanging tab 212 also allows outlet tubing 218 along with receiving blood bag 294 and air bag 295 to be coiled for shipping without kinking.

Figure 13:
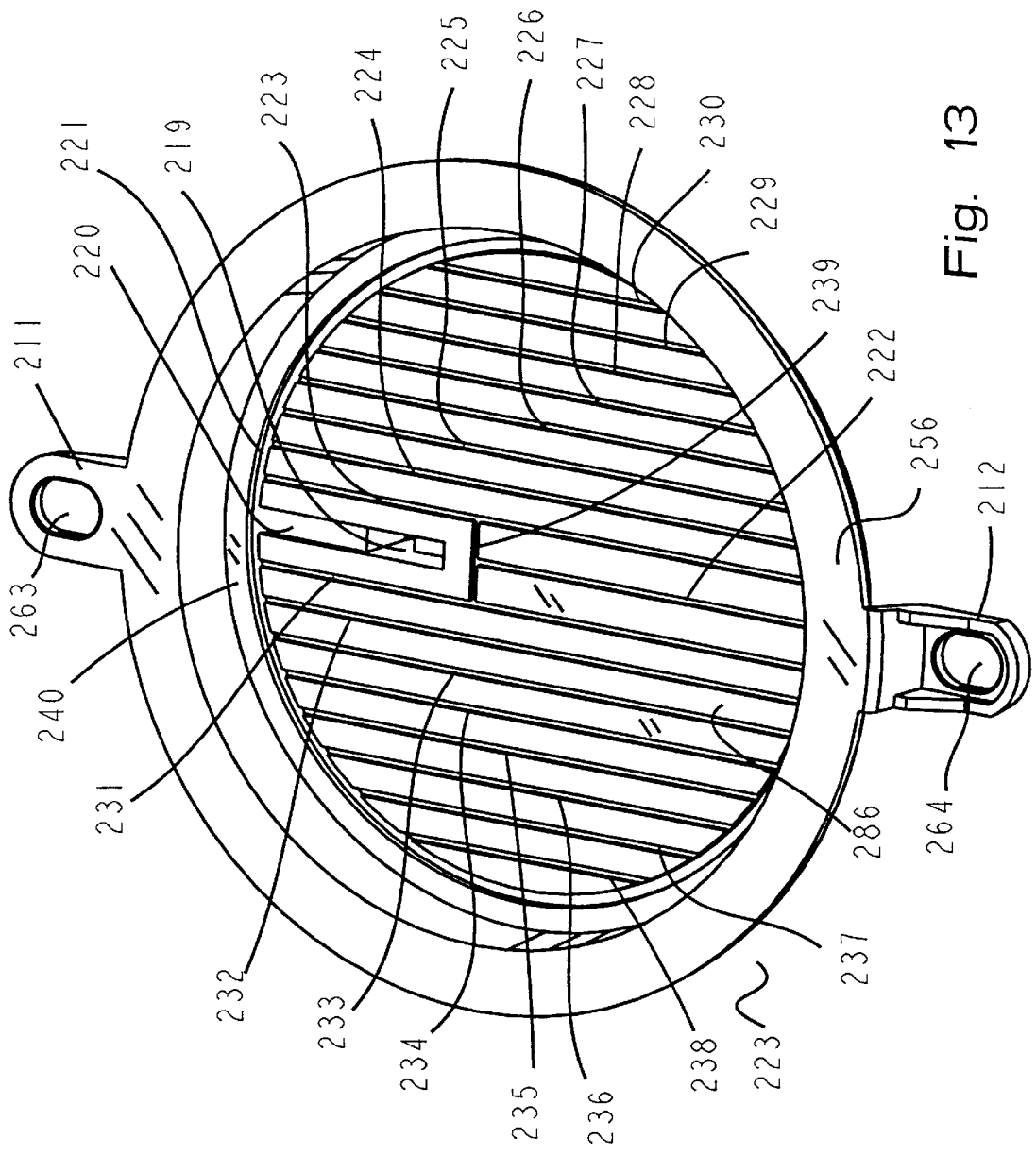
Figure 14:
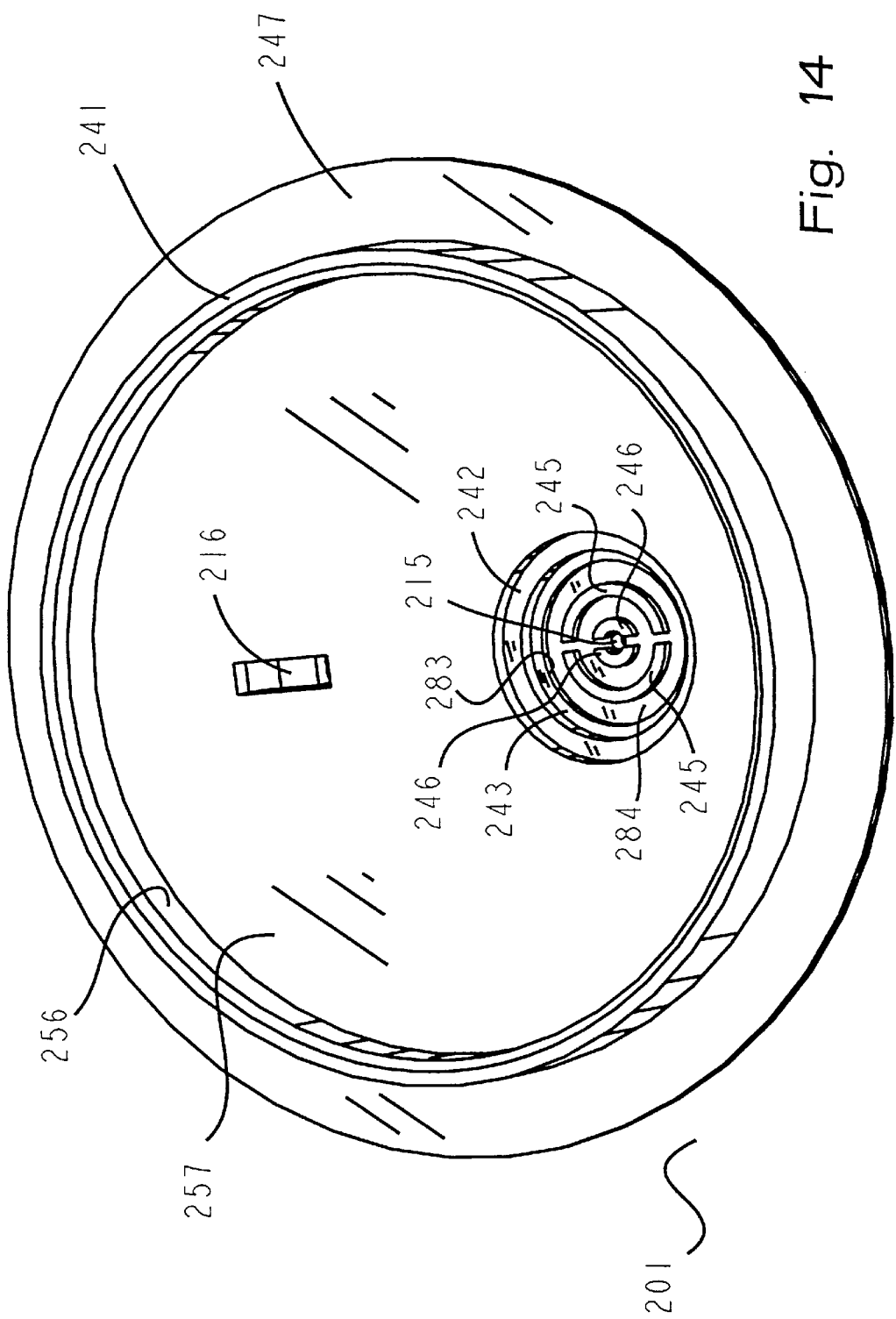
Figure 15:
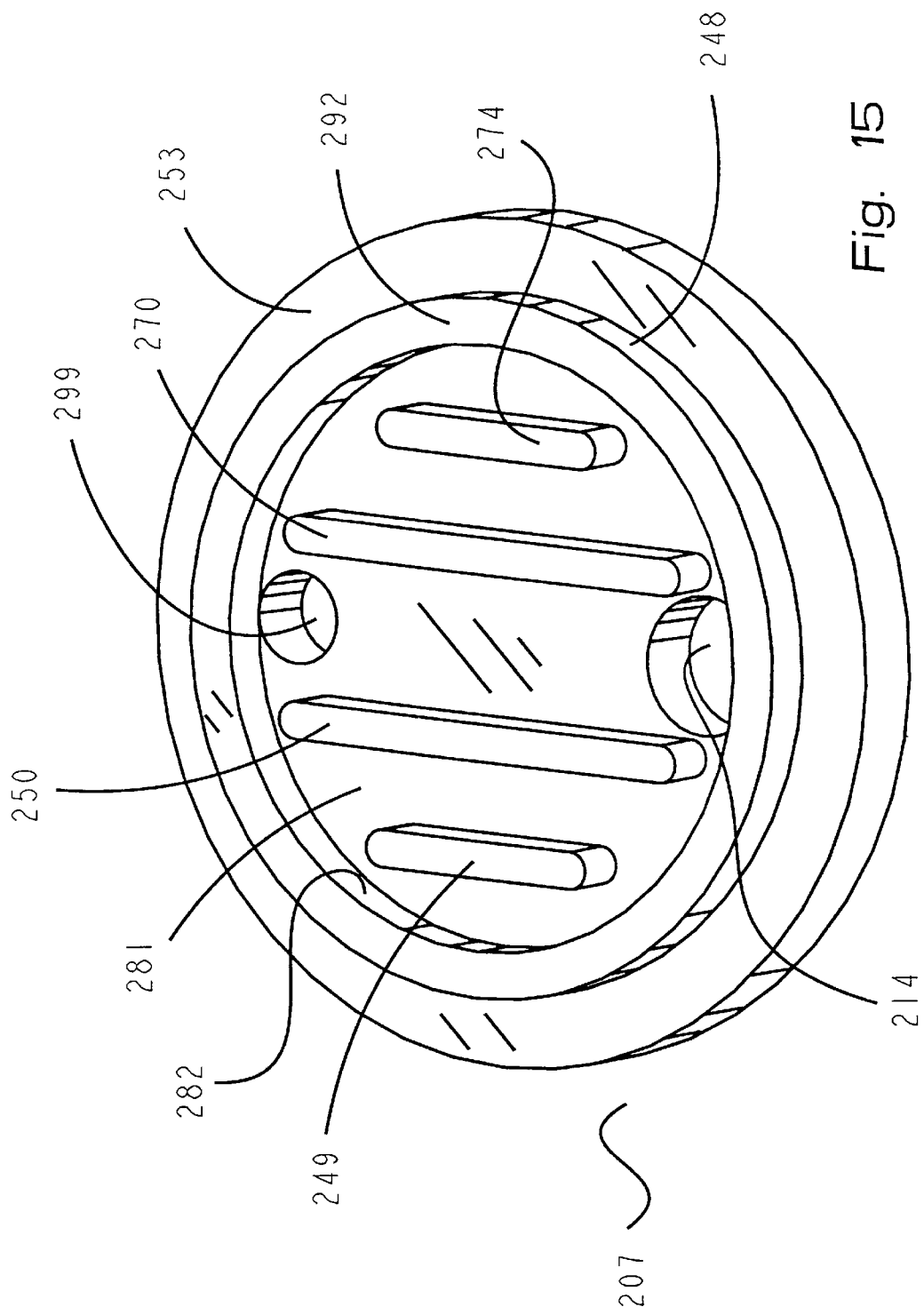

Referring to FIG. 13, the inside surface of outlet section 202 also contains channels 222 through 239, which are narrow and shallow and which are in fluid flow relationship with channel 221 which has a cross sectional area large enough to accommodate the combined flow from channels 222 through 239. Channel 221 is in fluid flow relationship with channel 220, which is in turn in fluid flow relationship with cavity 219, which is in fluid flow relationship with outlet tubing 218 through port 291. Channel 220 has a cross sectional area large enough to accommodate the flow from both sides of channel 221. It is important that as much of the filtered blood as possible be recovered in receiving blood bag 294. To minimize blood hold up in the filter support and drain structure that is made up of channels 220 through 239, the space between channels (for channels 222 through 238) should be much greater than the width of the channels. For example, the distance between channels is greater than four times the width of the channels. The ratio of distance between channels to channel width is dependent on the structure of filter element 206. The bottom of the last filter element (in this case filter element 206) contacts surface 286 of outlet section 202 and surface 240 of outlet section 202. Surfaces 286 and 240 are coplanar. Therefore, the bottom surface of filter element 206 closes off the top of channels 220 through 239.

Figure 17:
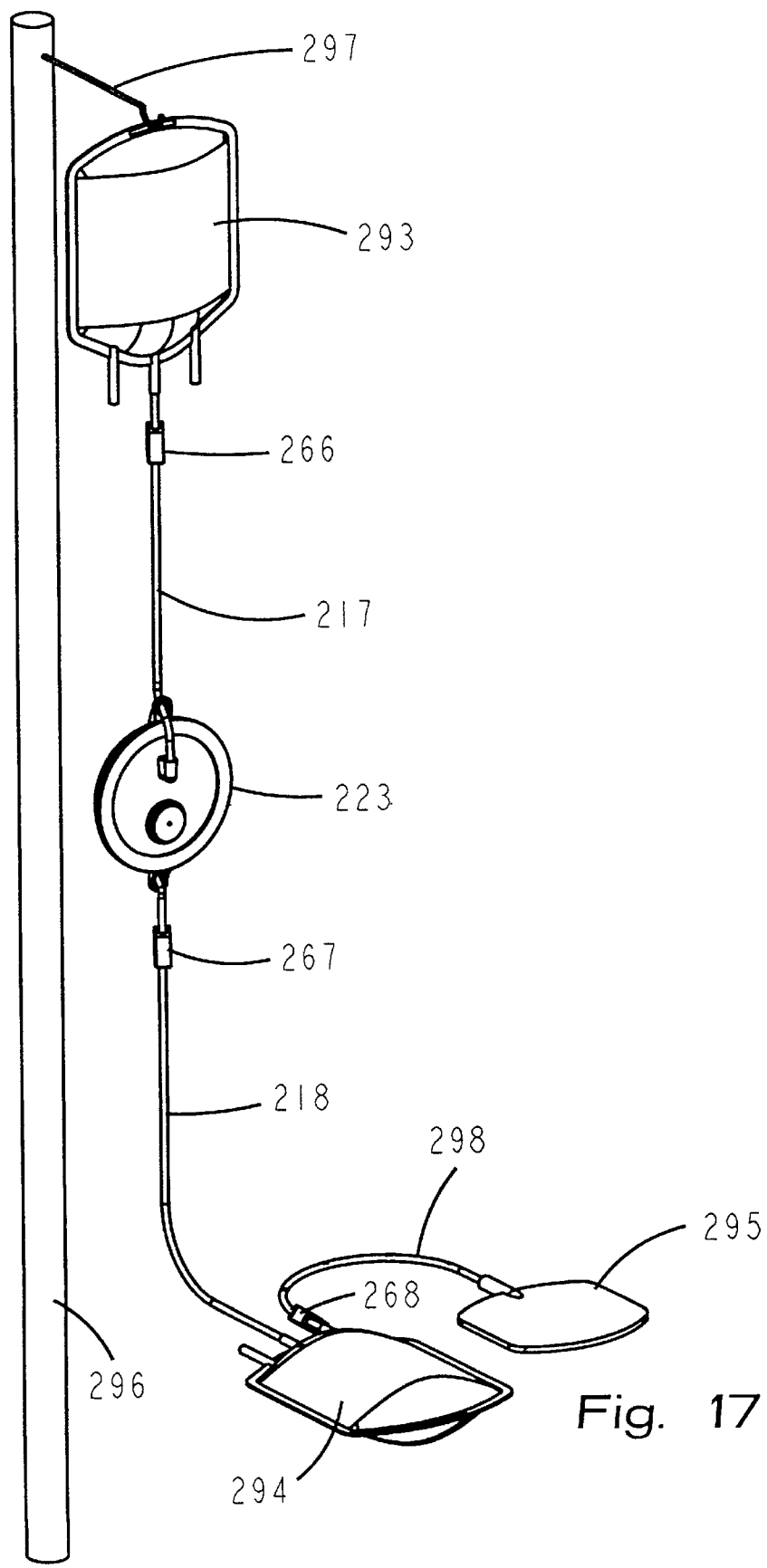

In FIG. 17 the filtration device 223 of FIG. 12 is depicted in operational assembly with inlet tubing 217, outlet tubing 218, feed blood bag 293, receiving blood bag 294, air bag 295, inlet tube clamp 266, outlet tube clamp 267, and air tube clamp 268. Preferably, the user will purchase the assembly of FIG. 17 sterilized without feed blood bag 293 with the inlet end of inlet tubing 217 sealed to maintain system sterility. For performing filtration, inlet tube clamp 266, located close to the inlet end of inlet tubing 217, is closed. Next the outlet tube clamp 267 is opened and air tube clamp 268, located close to the air tube port on receiving blood bag 294 is closed. Inlet tubing 217 (FIG. 12) attached to tube socket 287 above the center of inlet section 201 is now attached to a feed blood bag 293 using a sterile docking device as is well known in the art. Once the sterile docking connection is made feed blood bag 293 may be hung from hook 297 on blood bag pole 296. Receiving blood bag 294 and air bag 295 should be placed on a surface such as a table top or the like. The complete assembly ready for filtration is illustrated in FIG. 17. As depicted in FIG. 17, the inlet tube hanging tab 211 and outlet tube hanging tab 212 position inlet tubing 217 and outlet tubing 218 respectively so that filtration device 223 hangs vertical and plumb.

Referring to FIG. 12 and FIG. 17 filtration is performed as follows. Inlet tube clamp 266 is opened so that gravity now forces blood to flow from feed blood bag 293, through inlet tubing 217, through port 290 of inlet section 201, through cavity 216, into cavity 251 above the center of cavity 251. The air that was in inlet tubing 217 and cavity 216 will be pushed ahead of the blood, and will be forced into cavity 251. Cavity 251 will fill from the bottom up. Once the blood level in cavity 251 reaches the bottom of port 214 of vent insert 207 cavity 261 will begin to fill with blood. The blood level in cavity 261 will rise at the same rate as the blood level in cavity 251, until cavity 261 is filled with blood. The blood that initially fills cavity 261 will remain in cavity 261 for the remainder of the filtration process, because cavity 261 is dead ended. Only a very small volume of blood will contact hydrophobic filter 208 during the entire filtration process. Therefore, the fouling of the surface of hydrophobic filter 208 will be minimized, thus allowing the upstream side of filtration device 223 to drain quickly at the end of the filtration cycle. Once cavity 261 is filled with blood there will be a positive pressure in cavity 261. This positive pressure will prevent air from entering cavity 261 via port 215 of inlet section 201, and hydrophobic filter 208. The vent assembly that is made up of cavity 261, hydrophobic filter 208, cavity 262, port 215, port 214, and port 299 can be located any where on face 269 of inlet section 201. Hydrophobic filter 208 should be bacteria retentive, because the purpose of the vent assembly is to let air into the device when filtration is complete to drain the upstream side of the device, not to vent air out of the device, the volume of cavity 261 is not limited.

Cavity 251 of inlet section 201 will continue to fill until it is completely filled with blood. All of the air in cavity 251 above the top of port 299 of vent insert 207 will be forced through filter elements 203, 204, 205, and 206. All of the air that flows through filter elements 203, 204, 205, and 206 will flow into channels 220 through 239 (FIG. 13) and then flow through cavity 219, through port 291, into outlet tubing 218, into receiving blood bag 294. Filter elements 203, 204, 205, and 206 will also wet from the bottom up. The air that is initially in filter elements 203, 204, 205, and 206 will be displaced by blood and flow into channels 220 through 239 and then flow through cavity 219, through port 291, into outlet tubing 218, into receiving blood bag 294. Because the volume of cavity 251 is small, and the flow rate of blood entering cavity 251 from cavity 216 is much greater than the initial flow rate of blood through filter elements 203, 204, 205, and 206, cavity 251 will fill before filter elements 203, 204, 205, and 206 become completely wet with blood. The pressure head at the bottom of cavity 251 will be larger than the pressure head at the top of cavity 251, because of the height difference between the top and bottom of cavity 251. Therefore, liquid will start to come through filter element 206 from the bottom up. As liquid starts to come through filter element 206 from the bottom up, the channels in outlet section 202 will fill from the bottom up. Because the total volume of the channels in outlet section 202 is small (to minimize holdup) the channels may fill with blood (from the bottom up) before the upper part of filter element 206 has wet with blood. Once blood starts to flow from channel 220 of outlet section 202, into cavity 219 of outlet section 202, through port 290 of outlet section 202, into outlet tubing 218, and starts to flow down outlet tubing 218 toward receiving blood bag 294, the pressure in cavity 219 will become negative. Because channel 220 is in fluid flow relationship with cavity 219, the pressure inside the tube created by channel 220 and the bottom surface of filter element 206 will also be negative. Likewise since channel 221 is in fluid flow relationship with channel 220 the pressure inside the tube created by channel 221 and the bottom surface of filter element 206 will also be negative. Since the tube segments made up of channels 222 through 239 and the bottom surface of filter element 206 are in fluid flow relationship with the tube created by channel 221 and the bottom surface of filter element 206, any air or liquid that flows from filter element 206 into channels 222 through 239 will be sucked into channel 221, and then flow from channel 221 into channel 220, into cavity 219, through port 291, into outlet tubing 218, and into receiving blood bag 294. This assures that filter elements 203, 204, 205, and 206 will completely wet, and that all of the air that was in cavity 251 and filter elements 203, 204, 205, and 206 will be forced into receiving blood bag 294.

Blood filtration will continue until feed blood bag 293 is empty. When feed blood bag 293 is empty it will be collapsed and therefore close the inlet end of inlet tubing 217. Because outlet tubing 218 will be full of blood, and because the outside of receiving blood bag 294 is at atmospheric pressure, the pressure head in cavity 219 will be negative, as will be the pressure head in channels 220 through 239 of outlet section 202. Once blood flow has stopped the pressure drop across filter elements 203, 204, 205, and 206 will fall to zero. Hence the pressure in cavity 251 and cavity 261 will become negative. Once the pressure in cavity 261 falls below atmospheric pressure, air will begin to flow from atmosphere into port 215, through sterilizing grade hydrophobic filter 208, into cavity 261. This sterile air that enters cavity 261 from port 215 will bubble up to the top of cavity 261, through port 299 of vent insert 207, into cavity 251, and the bubble up to the top of cavity 251, thus draining cavity 251 from the top down. Once the blood level in cavity 251 falls to the top of port 299 of vent insert 207, cavity 261 will drain from the top down. The blood level in cavity 261 will fall at the same rate that the blood level falls in cavity 251. Once cavity 261 is completely drained cavity 251 will continue to drain until it is empty. Because the air entering cavity 251 from port 299 bubbles to the top of cavity 251, thus draining cavity 251 from the top down, the sub assembly consisting of cavity 261, cavity 262, port 215, and ports 214 and 299, can be located anywhere on face 269 of inlet section 201. The sub assembly consisting of cavity 261, cavity 262, port 215, and ports 214 and 299, can also be located above tube socket 287, and device 223 will function as described above. Filter elements 203, 204, 205, and 206 will be plugged sufficiently at this point so very little if any blood will be sucked from these filter elements by the negative pressure in channels 220 through 239. Hence blood flow will stop after cavity 251 has drained and blood will remain in filter elements 203, 204, 205, and 206, and in channels 220 through 239 of outlet section 202, and in cavity 219 of outlet section 202, and in outlet tubing 218.

Referring to FIG. 17, tube clamp 267, located between the filtration device 223 and the receiving bag 294, on outlet tubing 218 can be closed. Then tubing 218, above tube clamp 267, can be sealed using a conventional tube sealing device which is well known in the art and then cut above the seal. Feed blood bag 293, inlet tubing 217, and filtration device 223 can now be discarded in a safe manner. Tube clamp 268 opened so that air in receiving blood bag 294 can be expressed through air bag tubing 298 into air bag 295. Tube clamp 268 can now be closed and air bag tubing 298 sealed near the air bag 295. Air bag 295 can now be cut away above the seal just made and discarded in a safe manner. Therefore, receiving blood bag 294 with outlet tubing 218 and air bag tubing 298 now remain.

The filtration device illustrated in FIGS. 11 through 17 could be modified by eliminating port 299 of vent insert 207. The modified filtration device would function the same as the device described above with the exception that all of the air in cavity 261 would vent through port 215 to atmosphere when device 223 was filled with blood, and cavity 261 would drain before cavity 251 started to drain when filtration was complete.

The filtration device illustrated in FIGS. 11 through 17 could also be modified by eliminating vent insert 207. In this structure, cavity 261 would become a part of cavity 251, hence when liquid flow stops (i.e. when filtration is complete), air would flow from port 215 through cavity 262, through hydrophobic filter 208, directly into cavity 251, where it would bubble to the top of cavity 251, draining cavity 251 from the top down. However if vent insert 207 is eliminated, the blood flow around hydrophobic filter 208 will not be dead ended and hydrophobic filter 208 may clog more than it would if vent insert 207 is used. Vent insert 207 also provides filter support ribs 249, 250, 270, and 274, which support hydrophobic filter 208 when air flows from atmosphere, through port 215, through cavity 262, through hydrophobic filter 208, into cavity 261. Because hydrophobic filter 208 must be bacteria retentive it should be supported properly.

Figure 18:
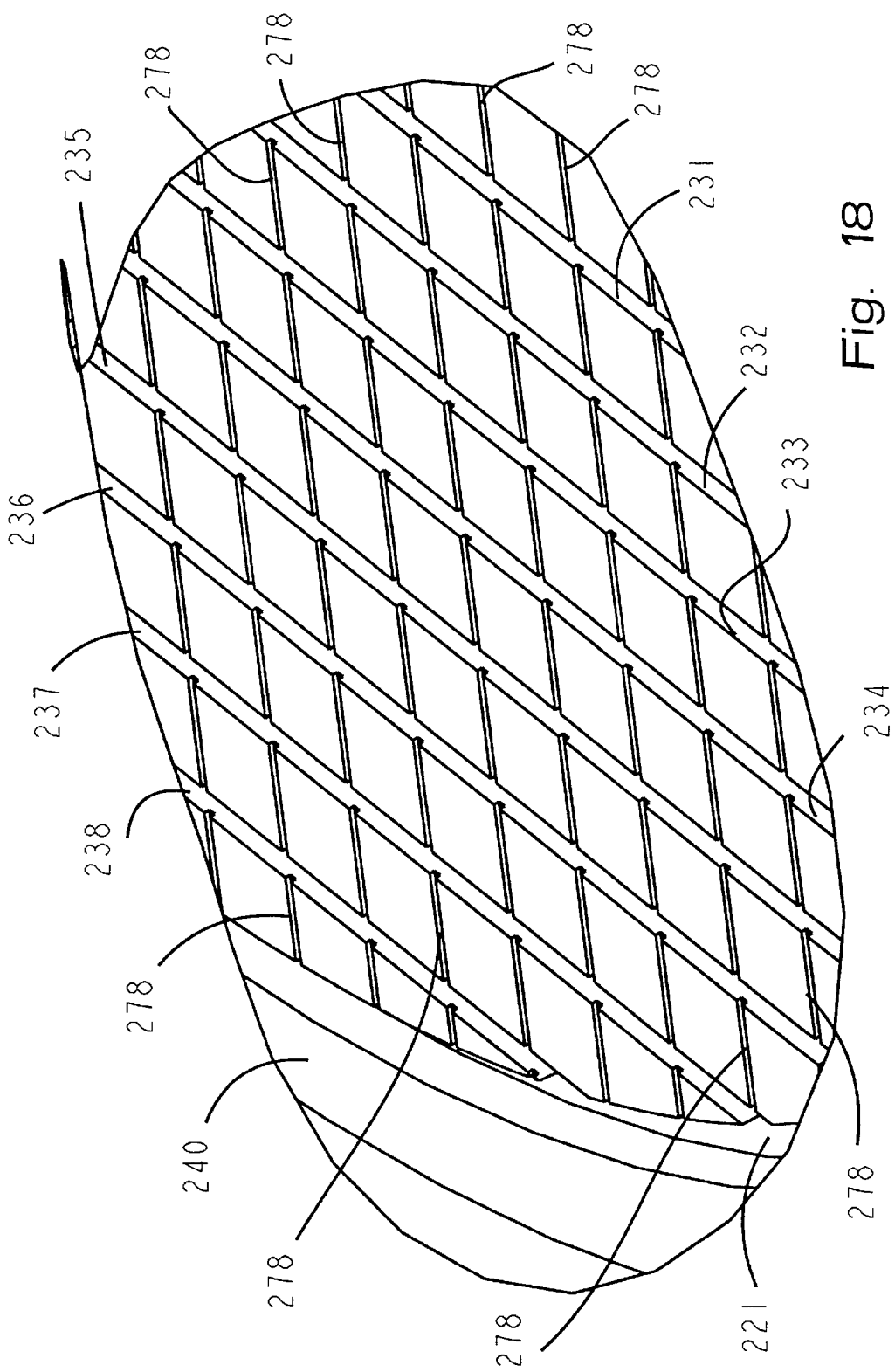

The filtration device of the present invention may be modified by adding the cross flow channels 278 as illustrated in FIG. 18 to the inside surface of the outlet section 2, 102, or 202. As used herein the term "cross flow channel" refers to a channel which drain into two or more parallel flow channels. The cross flow channels 278 should be narrower and shallower than channels 222 through 239. Cross flow channels 278 provide a means for the liquid exiting filter element 206 directly over the space 286 between channels 222 through 238 to flow into parallel flow channels 222–238. Because each segment of cross flow channel 278 provides a very short flow path for a very small cross sectional area of filter element 206, cross flow channels 278 may be narrower and shallower than parallel flow channels 222–238. Preferably the width of the cross flow channels should be less than or equal to the width of the parallel flow channels 222–238. Moreover, the depth of the cross flow channels 222–238 should be less than or equal to approximately half the depth of the parallel flow channels. The addition of cross channels 278 allows the space 286 between channels 222 through 238 to be maximized for a given type of filter element 206. Although cross channels 278 are shown to be rectangular in cross section, they may have other cross sections. Any pattern of shallow raised ridges or shallow channels that enhances the drainage of filter element 206 directly above space 286 between channels 222 through 238 may be used. The network of channels on the inside surface of the outlet section of the filtration device form a plurality of flow paths wherein any air or liquid therein is forced to flow further downstream and through the outlet of the device into the outlet tubing. Thus, no air pockets should remain on the downstream side of the device.

Although the invention has been described in conjunction with the embodiments depicted herein, it will be apparent to one of ordinary skill in the art that various modifications may be made to these embodiments without departing from the scope of the invention as defined in the following claims.

What is claimed is:

1. A method of preventing air from becoming entrapped within a filtration device of a biological liquid filtration system comprising:

flowing biological liquid through said filtration system and through said filtration device;

utilizing gravity to create a negative pressure downstream of a filtration media within said filtration device; and forcing air within said filtration device downstream of said filtration media to flow through an outlet at a flow rate sufficient to force air to flow into the outlet of said device and utilizing said negative pressure downstream of said filtration media to force air within said filtration device downstream of said filtration media to flow through said outlet after biological liquid flows through said outlet and at all times when biological liquid flows through said filtration media thereby preventing air from becoming trapped downstream of said filtration media within said filtration device.

2. The method of claim 1 further comprising forcing air located downstream of said filtration device to flow into a flow path comprising a first channel leading to said outlet of said device using filtered biological fluid.

3. The method of claim 2 further comprising flowing filtered biological liquid from a second channel into said first channel at a flow rate sufficient to force air from within said second channel into said first channel.

4. The method of claim 3 further comprising flowing filtered biological liquid from parallel channels into the second channel at a flow rate sufficient to force air from said parallel channels into said second channel.

5. The method of claim 4 further comprising flowing filtered biological liquid from cross flow channels into the parallel channels at a flow rate sufficient to force air therein into said parallel channels.

6. The method of claim 1 further comprising allowing biological liquid to remain within a tube located downstream of said filtration media.

7. The method of claim 1 wherein said biological liquid is filtered for the removal of cells.

8. The method of claim 1 wherein said biological liquid is filtered for the removal of chemical agents.

9. The method of claim 1 wherein said biological liquid is blood or a blood product.

10. The method of claim 1 further comprising letting air into the system through a vent assembly to drain biological liquid in the system when filtration is complete.

11. The method of claim 10, further comprising preventing the vent assembly from fouling with biological liquid.

12. The method of claim 11, further comprising preventing bacteria from entering the system.

13. The method of claim 10, wherein the vent assembly comprises a port located between an inlet and an outlet of the system and leading to outside of the system, the port being covered by a first hydrophobic filter and a second hydrophobic filter.

14. The method of claim 13, wherein the first hydrophobic filter is of a larger pore size than the second hydrophobic filter.

15. The method of claim 13, wherein the first hydrophobic filter prevents blood from fouling the second hydrophobic filter and the second hydrophobic filter is bacteria retentive.

16. A method of preventing air from becoming entrapped within a filtration device of a biological liquid filtration system comprising:

flowing biological liquid through said filtration system and through said filtration device;

forcing air within said filtration device downstream of a filtration media within said filtration device to flow into at least two non-periphery channels and into an outlet, wherein said non-periphery channels have distant opposite ends adjoining a common periphery channel of said filtration device; and forcing air within said filtration device downstream of said filtration media to flow through the outlet at a flow rate sufficient to force air to flow into the outlet of said device thereby preventing air from becoming trapped downstream of said filtration media within said filtration device.

17. The method of claim 16 further comprising forcing air located downstream of said filtration device to flow into a flow path comprising a first channel leading to said outlet of said device using filtered biological fluid.

18. The method of claim 17 further comprising flowing filtered biological liquid from a second channel into said first channel at a flow rate sufficient to force air from within said second channel into said first channel.

19. The method of claim 18 further comprising flowing filtered biological liquid from parallel channels into the second channel at a flow rate sufficient to force air from said parallel channels into said second channel.

20. The method of claim 19 further comprising flowing filtered biological liquid from cross flow channels into the parallel channels at a flow rate sufficient to force air therein into said parallel channels.

21. The method of claim 16 further comprising allowing biological liquid to remain within a tube located downstream of said filtration media.

22. The method of claim 16 wherein said biological liquid is filtered for the removal of cells.

23. The method of claim 16 wherein said biological liquid is filtered for the removal of chemical agents.

24. The method of claim 16 wherein said biological liquid is blood or a blood product.

25. The method of claim 1, wherein said negative pressure comprises flowing filtered biological liquid through the outlet before the filtration media is substantially completely wet with biological liquid.

26. The method of claim 16, further comprising creating a negative pressure downstream of said filtration media.

* * * * *